United States Patent
Copa et al.

(10) Patent No.: US 8,808,232 B2
(45) Date of Patent: Aug. 19, 2014

(54) NEEDLELESS DELIVERY SYSTEMS

(75) Inventors: Vincent G. Copa, Minnetonka, MN (US); Sidney F. Hauschild, St. Paul, MN (US)

(73) Assignee: AMS Research Corporation, Minnetonka, MN (US)

( * ) Notice: Subject to any disclaimer, the term of this patent is extended or adjusted under 35 U.S.C. 154(b) by 3 days.

(21) Appl. No.: 13/569,788

(22) Filed: Aug. 8, 2012

(65) Prior Publication Data

US 2012/0302827 A1 Nov. 29, 2012

Related U.S. Application Data

(62) Division of application No. 11/186,218, filed on Jul. 21, 2005.

(60) Provisional application No. 60/634,974, filed on Dec. 9, 2004.

(51) Int. Cl.
*A61M 5/30* (2006.01)

(52) U.S. Cl.
USPC ............. 604/70; 604/218; 604/509; 604/524; 604/101.01; 604/101.05; 604/121; 604/141; 604/144; 600/101; 600/114; 600/115; 600/117

(58) Field of Classification Search
USPC ............. 600/104, 114, 115, 117; 604/101.01, 604/101.05, 121, 141, 144, 218, 509, 524
See application file for complete search history.

(56) References Cited

U.S. PATENT DOCUMENTS

| | | | |
|---|---|---|---|
| 2,499,045 A | 2/1950 | Frank et al. | |
| 2,687,131 A | 8/1954 | Raiche | |
| 3,425,413 A | 2/1969 | Stephens | |
| 3,635,223 A | 1/1972 | Klieman | |
| 3,905,361 A | 9/1975 | Hewson et al. | |
| 4,116,201 A | 9/1978 | Shah | |
| 4,126,134 A | 11/1978 | Bolduc et al. | |

(Continued)

FOREIGN PATENT DOCUMENTS

| | | |
|---|---|---|
| WO | WO 00/67647 | 11/2000 |
| WO | WO 03/030756 | 4/2003 |

OTHER PUBLICATIONS

Watson, Patel & DiTrolio, "Transurethral Ethanol Ablation of the Prostate," The Journal of Urology, vol. 161, No. 4, Supplement, p. 305, Apr. 1999.

(Continued)

*Primary Examiner* — Nicholas Lucchesi
*Assistant Examiner* — Scott Medway
(74) *Attorney, Agent, or Firm* — Kagan Binder, PLLC

(57) ABSTRACT

A needleless injector including a body including a fluid chamber; an outer shaft extending from an outer shaft proximal end to an outer shaft distal end, wherein the outer shaft includes an outer shaft lumen to accommodate an injection shaft; an injection shaft located within the outer shaft lumen and moveable lengthwise and/or rotationally within the outer shaft lumen, wherein the injection shaft includes an injection shaft proximal end, an injection shaft distal end, an injection shaft terminus, and an injection lumen. The injector further includes an injection orifice at the distal end of the injection shaft and in fluid communication with the fluid chamber through the injection lumen; a pressure source in communication with the fluid chamber; and an optical device that allows viewing a location at a distal end of the device.

7 Claims, 12 Drawing Sheets

(56) References Cited

U.S. PATENT DOCUMENTS

| | | | |
|---|---|---|---|
| 4,417,576 | A | 11/1983 | Baran |
| 4,423,725 | A | 1/1984 | Baran et al. |
| 4,430,076 | A | 2/1984 | Harris |
| 4,461,283 | A | 7/1984 | Doi |
| 4,636,195 | A | 1/1987 | Wolinsky |
| 4,763,654 | A | 8/1988 | Jang |
| 4,811,847 | A | 3/1989 | Reif et al. |
| 4,827,907 | A | 5/1989 | Tashiro |
| 4,867,742 | A | 9/1989 | Calderon |
| 4,958,634 | A | 9/1990 | Jang |
| 4,985,022 | A * | 1/1991 | Fearnot et al. ............... 604/288 |
| 4,994,033 | A | 2/1991 | Shockey et al. |
| 5,009,659 | A | 4/1991 | Hamlin et al. |
| 5,033,998 | A | 7/1991 | Corday et al. |
| 5,087,244 | A | 2/1992 | Wolinsky et al. |
| 5,112,305 | A | 5/1992 | Barath et al. |
| 5,158,540 | A | 10/1992 | Wijay et al. |
| 5,221,258 | A | 6/1993 | Shturman |
| 5,257,977 | A | 11/1993 | Eshel |
| 5,279,565 | A | 1/1994 | Klein et al. |
| 5,282,785 | A | 2/1994 | Shapland et al. |
| 5,322,503 | A | 6/1994 | Desai |
| 5,336,178 | A * | 8/1994 | Kaplan et al. ............... 604/509 |
| 5,419,763 | A * | 5/1995 | Hildebrand ............... 604/517 |
| 5,423,745 | A | 6/1995 | Todd et al. |
| 5,441,485 | A | 8/1995 | Peters |
| 5,458,571 | A | 10/1995 | Lampropoulos et al. |
| 5,464,395 | A | 11/1995 | Faxon et al. |
| 5,501,666 | A | 3/1996 | Spielberg |
| 5,562,703 | A | 10/1996 | Desai |
| 5,569,219 | A | 10/1996 | Hakki |
| 5,637,086 | A | 6/1997 | Ferguson et al. |
| 5,693,029 | A | 12/1997 | Leonhardt |
| 5,746,716 | A | 5/1998 | Vigil et al. |
| 5,823,940 | A | 10/1998 | Newman |
| 5,840,061 | A | 11/1998 | Menne et al. |
| 5,861,002 | A | 1/1999 | Desai |
| 5,904,147 | A | 5/1999 | Conlan et al. |
| 5,919,163 | A | 7/1999 | Glickman |
| 5,938,637 | A * | 8/1999 | Austin et al. ............... 604/72 |
| 5,964,756 | A | 10/1999 | McGaffigan et al. |
| 6,048,332 | A | 4/2000 | Duffy et al. |
| 6,102,896 | A * | 8/2000 | Roser ............... 604/218 |
| 6,132,395 | A | 10/2000 | Landau et al. |
| 6,159,141 | A | 12/2000 | Apple et al. |
| 6,231,591 | B1 | 5/2001 | Desai |
| 6,280,414 | B1 | 8/2001 | Shah et al. |
| 6,283,947 | B1 | 9/2001 | Mirzaee |
| 6,344,027 | B1 | 2/2002 | Goll |
| 6,358,197 | B1 | 3/2002 | Silverman et al. |
| 6,440,099 | B2 | 8/2002 | Haar et al. |
| 6,461,296 | B1 | 10/2002 | Desai |
| 6,514,247 | B1 | 2/2003 | McGaffigan et al. |
| 6,602,241 | B2 | 8/2003 | Makower et al. |
| 6,607,510 | B2 | 8/2003 | Landau |
| 6,641,553 | B1 | 11/2003 | Chee et al. |
| 6,645,170 | B2 | 11/2003 | Landau |
| 6,709,427 | B1 | 3/2004 | Nash et al. |
| 6,716,190 | B1 | 4/2004 | Glines et al. |
| 6,752,781 | B2 * | 6/2004 | Landau et al. ............... 604/70 |
| 6,905,475 | B2 | 6/2005 | Hauschild et al. |
| 6,939,381 | B2 | 9/2005 | Stark et al. |
| 6,964,649 | B2 | 11/2005 | Goll |
| 6,974,441 | B2 | 12/2005 | Ravo |
| 6,994,667 | B2 * | 2/2006 | Singh ............... 600/105 |
| 7,015,253 | B2 | 3/2006 | Escandon et al. |
| 7,060,051 | B2 | 6/2006 | Palasis |
| 7,147,633 | B2 | 12/2006 | Chee |
| 7,182,745 | B2 | 2/2007 | Desmond, III |
| 7,419,482 | B2 | 9/2008 | Nash et al. |
| 7,517,352 | B2 | 4/2009 | Evans et al. |
| 2002/0183738 | A1 * | 12/2002 | Chee et al. ............... 606/41 |
| 2003/0191449 | A1 | 10/2003 | Nash et al. |
| 2004/0111055 | A1 | 6/2004 | Daellenbach |
| 2004/0193097 | A1 | 9/2004 | Hofmann et al. |
| 2009/0312696 | A1 * | 12/2009 | Copa et al. ............... 604/43 |

OTHER PUBLICATIONS

DiTrolio, J.V., "Chemoablation of the Prostate with Dehydrated Ethanol for the Treatment of BPH," presented at the 5$^{th}$ International Consultation on BPH, Paris, France, Jun. 2000.

* cited by examiner

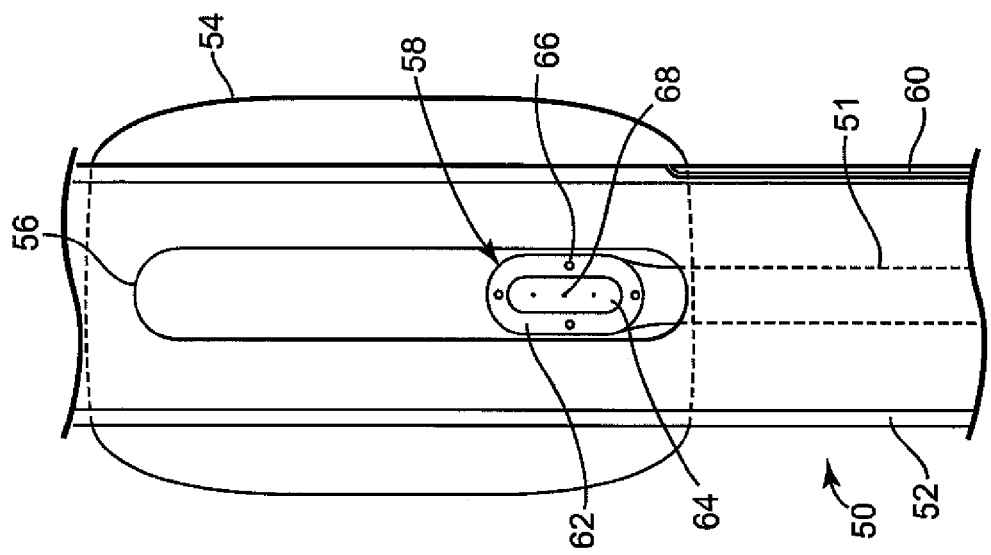
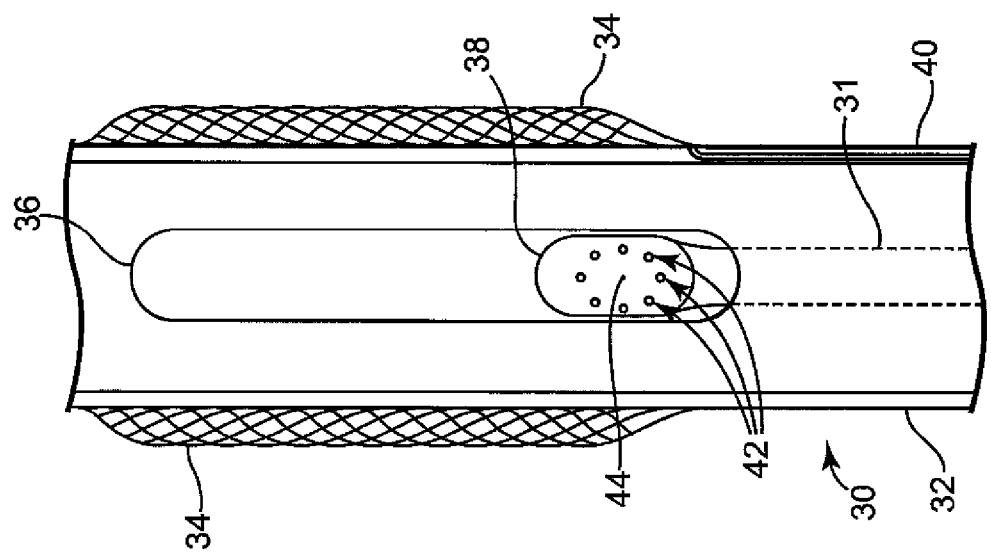

NEEDLELESS DELIVERY SYSTEMS

CROSS-REFERENCE TO RELATED APPLICATION

The present patent application is a divisional application of U.S. patent application Ser. No. 11/186,218, filed Jul. 21, 2005, which claims the benefit under 35 U.S.C. §119(e) of U.S. Provisional Patent Application No. 60/634,974, filed on Dec. 9, 2004, the entire disclosures of which are incorporated herein by reference in their entireties.

FIELD OF THE INVENTION

The invention relates to methods and devices for treating tissue of the lower urinary tract (e.g., prostate tissue, kidneys, ureters, urethral tissue, bladder, etc.), as well as devices, methods, and surgical kits for use in a treatment regimen.

BACKGROUND

Lower urinary tract health is an increasingly important health issue, e.g., based on an aging population. Treatment of lower urinary tract conditions is an area of much investigation.

Prostate disease, for example, is a significant health risk for males. Diseases of the prostate include prostatitis, benign prostatic hyperplasia (BPH, also known as benign prostatic hypertrophy), and prostatic carcinoma.

Prostatitis is an inflammation of the prostate gland. Types include acute and chronic bacterial forms of prostatitis, and a non-bacterial form. Symptoms can include difficult urination, burning or painful urination, perineal or lower back pain, joint or muscle pain, tender or swollen prostate, blood in the urine, or painful ejaculation. Prostatitis is caused by bacterial infection in many instances, in which case treatment generally includes antimicrobial medication. Noninfectious forms of prostatitis are treated by other means such as administration of an alpha-1-adrenoreceptor antagonist drug to relax the muscle tissue in the prostate and reduce the difficulty in urination.

Benign prostatic hypertrophy (BPH) is a very common disorder affecting an estimated 12 million men in the United States alone. BPH is a chronic condition and is strongly age-related; approximately 50% of men over the age of fifty, 75% of men beyond the age of seventy, and 90% of men over the age of eighty are afflicted with BPH. BPH is a non-cancerous condition characterized by enlargement of the prostate, obstruction of the urethra, and gradual loss of bladder function. Symptoms include difficult urination, frequent urination, incomplete emptying of the bladder, and urgency.

BPH may be treated with a number of therapeutic modalities including surgical and medical methods, depending on severity of symptoms. Treatments range from "watchful waiting" for men with mild symptoms, to medications, to surgical procedures. Examples of useful medications include 5-alpha reductase inhibitors such as Avodart™ and Proscar®.

Transurethral resection of the prostate (TURP) is a preferred surgical method of treating BPH. A typical TURP procedure requires general anesthesia and the placement of a resectoscope in the urethra for removal of multiple small chips of hyperplastic prostatic tissue to relieve the obstruction. Complications from TURP include bleeding, incontinence, retrograde ejaculation, and impotence.

An alternate surgical method for treating BPH is transurethral incision of the prostate (TUIP). In the TUIP procedure, incisions are made in the prostate to relieve pressure and improve flow rate. Incisions are made where the prostate meets the bladder. No tissue is removed in the TUIP procedure. Cutting muscle in this area relaxes the opening to the bladder, which decreases resistance to urine flow from the bladder. A variant of the TUIP procedure in which a laser is used to make the incision is known as transurethral laser incision of the prostate (TULIP).

Other surgical methods used to relieve the symptoms of BPH include methods of promoting necrosis of tissue that blocks the urethra. Hyperthermic methods, for example, use the application of heat to "cook" tissue and kill the cells. The necrosed tissue is gradually absorbed by the body. Several methods of applying heat or causing necrosis have been demonstrated, including direct heat (transurethral needle ablation, or TUNA), microwave (transurethral microwave treatment, or TUMT), ultrasound (high-intensity focused ultrasound, or HIFU), electrical vaporization (transurethral electrical vaporization of the prostate, or TUEVP) and laser ablation (visual laser ablation of the prostate, or VLAP), among others.

Chemical ablation (chemoablation) techniques for promoting prostate tissue necrosis have also been considered. In one chemical ablation technique, absolute ethanol is injected transurethrally into the prostate tissue. This technique is known as transurethral ethanol ablation of the prostate (TEAP). The injected ethanol causes cells of the prostate to burst, killing the cells. The prostate shrinks as the necrosed cells are absorbed.

SUMMARY

The invention relates to needleless devices useful for injecting fluid to tissue of the lower urinary tract such as the prostate. The devices inject a therapeutic fluid or "injectate" at high-pressure using an orifice at the end of an elongate shaft inserted into the urethra. To treat the prostate, the injectate fluid passes through the urethra and disperses in the prostate as a cloud of particles.

Various treatments of the prostate that are currently used or proposed, such as transurethral chemical ablation or administering an active pharmaceutical, involve injection of a therapeutic fluid into the prostate using a needle located in and passed through the urethra. The use of a needle to inject a therapeutic fluid such as a drug or ethanol can involve various difficulties or undesired effects due to the structure of the prostate and the manner and nature by which a needle delivers a fluid by injection.

Generally, injection using a needle is inherently susceptible to flow of a liquid injectate back through the tissue path created by the needle, i.e., "backflow." Fluid that is pressurized to flow from the tip of the needle into desired tissue can flow back out of the tissue through the path of the needle causing that amount of the liquid to be ineffective in treating the targeted tissue.

Specifically with respect to injecting the prostate, this organ has a glandular structure that contains its own fluid ducts for channeling biological fluids to the urethra. When injecting fluid to the prostate gland using a needle, the utility and performance of a needle is limited in that a needle can inject a volume of fluid only at a discrete location ("bolus") in the prostate. An injected volume of fluid can typically produce a pool (bolus) of fluid at the injection site at the needle tip. This pool collects at an isolated location within the highly ducted structure of the prostate. The pool of injected fluid will naturally flow through the ducted structure of the prostate leading out of the prostate and into the urethra where the fluid is not desired or effective.

A result of the pooling of an injectate delivered to a prostate using a needle, and the undesired flow of the injectate through ducts of the prostate, is that a substantially larger volume of injectate must be delivered for treatment because much of the injectate is carried away from the desired treatment site within the prostate. The total amount of fluid delivered must account for the amount that is therapeutically effective and the additional amount that is lost, meaning that a larger total volume of fluid must be injected, i.e., an overdose.

Another disadvantage of the use of a needle to inject fluid into the prostate is that an injection through a needle must be delivered slowly, to minimize back-pressure and consequent pooling of the injected fluid during injection into the prostate, and to avoid backflow of the injectate along the tissue path of the needle.

The invention relates to devices, systems, and methods for using a needleless system for transurethral injection of a fluid ("injectate") to tissue of the lower urinary tract, such as the prostate. The needleless systems can overcome undesired or disadvantageous features of systems and methods that use a needle, e.g., for transurethral injections of fluid into the prostate.

A needleless injection does not cause an injected fluid to pool at a locality within injected tissue as does injection of a fluid using a needle. As opposed to a pool of fluid, a fluid that is injected into tissue by a needleless injection system becomes dispersed as droplets or particles of liquid that enter an injected tissue and disperse within the tissue. The injected fluid, in the form of droplets, does not flow into pools that could allow for backflow through a tissue path or that could potentially reach a gland duct to flow, e.g., from the prostate into the urethra. Preferably, an injectate delivered by needleless injection can be in the form of a fine mist that advantageously is distributed as a cloud of particles or droplets throughout injected tissue.

An attendant advantageous effect of a needleless injection compared to the use of a needle is that the total amount of fluid injectate is reduced because there is no loss from flow out of the injected tissue. There is no need for "overdosing" as with the use of a needle.

A needleless mode of injecting a fluid into the prostate or other tissue of the lower urinary tract requires that certain technical challenges be overcome to accommodate the specific technical and medical needs of injecting a therapeutic fluid to internal tissue, optionally transurethrally, without a needle. For instance, to inject the prostate, a needleless injector must be of a size and shape that may be placed within the urethra while also providing an injectate at the injection orifice in the prostatic urethra at a pressure sufficient to penetrate urethral and prostate tissues. The injectate must penetrate urethral and prostate tissues in a predictable and desired fashion to become dispersed throughout the prostate tissue.

A particular need for delivery of a therapeutic fluid to tissue of the lower urinary tract is that the injected fluid must be delivered at distance (i.e., "throw") from a pressurized source of fluid. Specifically, the delivery site is a distance from the source of the therapeutic fluid, through a length of shaft, and the delivery may be in a direction that includes a directional component directed away from the longitudinal axis of the shaft, i.e., delivery may be performed away from the tip of a shaft and in a direction that is not the same as the axis of the shaft.

Additionally, injected fluid is desirably dispersed throughout the injected tissue. Needleless delivery of a therapeutic fluid to prostate tissue, for example, is best if the therapeutic agent is dispersed uniformly throughout the prostate as droplets or particles. An enlarged prostate is not typically enlarged homogeneously but includes isolated enlarged nodules potentially throughout. The location of the enlarged portions are not typically precisely known, so it is considered good treatment practice to disperse therapeutic agent throughout the entire prostate.

Furthermore, the location of the lower urinary tract as internal organs, and delivery optionally through the urethra, result in an importance to being able to precisely position a needleless injection orifice for injecting a fluid. Particularly desirable features of a needleless injector may include features that facilitate placement of injection orifices at desired locations for injection, e.g., an optical device that allows for viewing of internal tissue.

Still additionally, inadvertent, misplaced, or incorrect actuation of a needleless injection system at a time when the system is installed or partially installed, would normally result in severe injury to urethral tissue, prostate tissue, or any other tissue exposed to an incorrectly-performed injection. For instance if an injection mechanism were actuated when a needleless injector device does not properly contain a liquid in the injection lumen, causing air to be ejected, great injury would result to affected tissues. As such, safety features that prevent inadvertent or incorrect actuation of the injection mechanism are very important.

Features of needleless injector devices described above are included as part of the present disclosure and may be included in a needleless injector device individually or in any desired combination. For example, embodiments of the invention include needleless injector devices that include positioning features that facilitate proper positioning of an injection orifice in the urethra. Positioning features are various in nature and may include one or more of: a balloon or multiple balloons located at the distal end of the device for placement and fixing the distal end; multiple orifices; moveable orifices; demarcation of distances to distal end features, at the proximal end; and an optical feature such as an endoscope or optical fiber. Other embodiments of needleless injector devices include the above features along with one or more tissue tensioners that contact and optionally place pressure on tissue at a desired location relative to an injection orifice, and optionally can also place a strain or tension on the tissue as desired for delivery of an injection at the surface of the tissue. Examples of tissue tensioners include inflatable or extendable features such as balloons or mechanically extendable features such as paddles, metal cages, other mechanically extendable protrusions, vacuum, etc.

Needleless injector devices as described can be used with various delivery methods such as methods that allow for direct vision of an injection wherein an internal location of an injection orifice is determined visually, and methods referred to as blind delivery methods wherein location of an injection orifice is determined indirectly. Direct vision methods involve the use of an optical feature to view an injection site directly, such as by use of an endoscope or optical fiber that is included in an injector device, e.g., as a component of the shaft. A device that allows for blind delivery can instead include one or more non-optical features that allow a surgeon to identify the position of a device, and in particular an injection orifice, e.g., within the urethra, so that an injection can be performed at a desired location. Blind delivery techniques can identify a delivery location based on features of the device such as a length-measuring feature such as demarcations at the proximal end of the device that reference locations of features at the distal end, by using demarcations in combination with known dimensions of a device and of anatomy. Demarcations may be used also in combination with measurement of anatomical features such as the length of the prostate, e.g., by known techniques including those that use ultrasound position measuring equipment. Blind delivery techniques can also involve other features of devices as described herein such as positioning features (e.g., balloons at the distal end of the device) and moveable injection orifices.

Various embodiments of injector devices of the invention can include different types of shafts, including a flexible shaft, a rigid shaft, a multi-piece shaft designed to be assembled and disassembled prior to or following use, and an integral shaft that is not designed to be assembled and disassembled prior to or after use. Particular devices and methods of the invention involve shafts that are flexible integral shafts wherein the device does not include an optical device such as an endoscope but includes positioning features such as balloons, and is used with blind delivery methods. Other devices and methods involve multi-component shafts that include an endoscope and other features as described herein.

Various embodiments of the invention can optionally or alternately include safety features that prevent inadvertent or improper ejection of fluid from a device, and features that add convenience or efficiency such as trigger mechanisms, systems and methods that allow for multiple injections, methods of controlling or programming volumes, depths, or other features of one or multiple injections.

An aspect of the invention relates to a needleless injector device. The device includes a body at a proximal end; a shaft extending from the body to a distal end of the shaft; an injection orifice at the distal end of the shaft in fluid communication with a fluid chamber at the proximal end, the injection orifice directed away from the longitudinal axis of the shaft; a pressure source in communication with the fluid chamber, and a tissue tensioner located at the distal end of the shaft proximal to the injection orifice.

Another aspect of the invention relates to a needleless injector device that includes a body at a proximal end; a flexible shaft extending from the body to a distal end of the shaft; an injection orifice at the distal end of the shaft in fluid communication with a fluid chamber at the proximal end; and a pressure source in communication with the fluid chamber.

Yet another embodiment of the invention relates to a needleless injector device that includes a body having a fluid chamber; a shaft extending from the body to a distal end of the shaft; an injection orifice at the distal end of the shaft; an injection lumen connecting the injection orifice and the fluid chamber; and a priming mechanism capable of filling the injection lumen by low pressure flow of fluid from the fluid chamber.

BRIEF DESCRIPTION OF THE DRAWINGS

FIGS. 2 and 2a illustrate exemplary components of a shaft of an injector device, including tissue tensioning features and features of injector heads.

FIGS. 3 and 3a illustrate exemplary components of a shaft of an injector device, including tissue tensioning features and features of injector heads.

Figure 1:
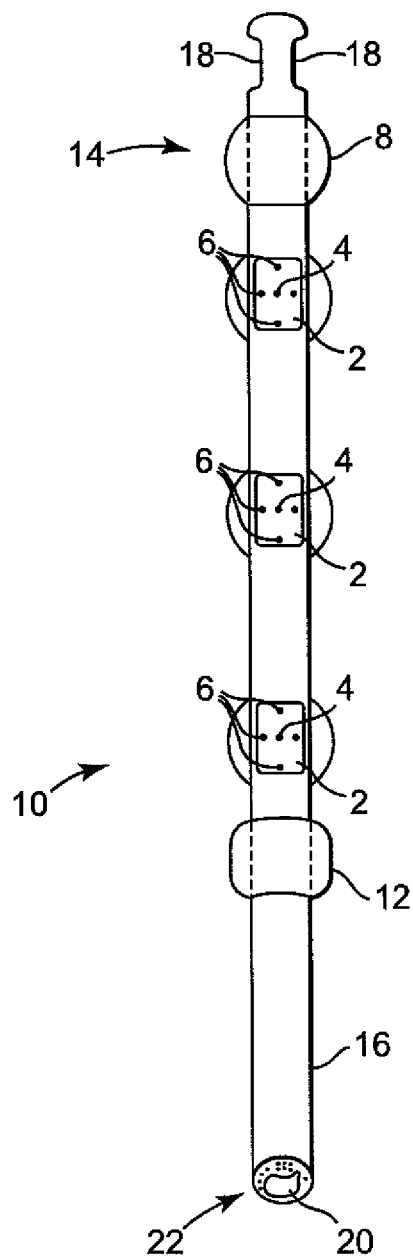
FIG. 1 illustrates an exemplary components of a shaft of an injector device of the invention.

All drawings are schematic and not necessarily to scale.

DETAILED DESCRIPTION

Devices, systems, and methods are provided that allow for needleless injection of a therapeutic fluid ("injectate"). The devices may be used for various applications related to conditions of a lower urinary tract such as the urethra, bladder, kidney, ureters, prostate, etc. In one particular method an injectate such as a pharmaceutical or ablative agent can be injected transurethrally, without a needle, into the prostate. The devices are designed to place an injection orifice at a desired location within the lower urinary tract to allow needleless transurethral delivery (i.e., injection) of therapeutic fluid to desired tissue.

The invention identifies and addresses certain practical problems associated with other modes of injecting fluid into tissue of the lower urinary tract. For example, injection of fluid to the prostate by use of a needle can cause pooling of fluid in the highly-ducted structure of the prostate resulting in undesired flow of the fluid away from the intended therapeutic location in the prostate. Needleless injector devices and methods as described herein are advantageous compared to the use of a needle for various reasons including that the needleless injection produces an injection in the form of a cloud of dispersed particles of injectate that penetrates the injected tissue and disperses. Advantageously, these injected particles do not pool.

The devices and methods include various features discussed herein, any of which can be used either separately or in combination with any one or more of the other described features. The features include the following: construction of a shaft of the device in multiple, separable pieces, or as a single "integral" piece; a rigid shaft or a flexible shaft; features relating to the number and positioning of injection orifices such as multiple injection orifices located at different positions along a length of a shaft of a device or located at different positions around a perimeter of a shaft of the device, and moveable injection orifices that may be moveable along a length of a shaft, around a perimeter of a shaft, or along a length and around a perimeter of the shaft; one or more tissue tensioners to contact tissue near an injection orifice and manipulate the tissue as desired during injection; locating features such as balloons or other mechanisms to fix the location of a portion of a device, e.g., within the urethra; safety features that prevent inadvertent or improper actuation of a device or ejection of fluid from a device; and features that add convenience or efficiency such as specific trigger mechanisms, systems and methods that allow for multiple injections or dosages, and methods and features for controlling or programming volumes, depths, timing, order, positioning, or other features of one or multiple injections.

Generally, an injector device can include a body at a proximal end, the body including one or more fluid chambers. A shaft is attached to the body. A fluid chamber can be a fluid reservoir, a syringe chamber, or a device may include both. A reservoir can refer to a fixed-volume holding space for injectate fluid and need not (but may) be capable of being pressurized to low or moderate pressure or highly pressurized, e.g., pressurized to allow for priming or to cause injectate fluid to be ejected from an injection orifice by way of an injection lumen. A reservoir can be sized to contain one or multiple volumes of injectate, and may be in the form of a removable or replaceable vial.

Another exemplary type of fluid chamber is referred to as a syringe chamber, which is a chamber that has a variable volume based, e.g., on a plunger, piston, bellows, or other mechanism for increasing or decreasing the volume (and pressure) of the chamber. A syringe chamber can be pressurized by a pressure source attached to the plunger, bellows, or piston such that injectate fluid contained in the syringe chamber is ejected under pressure from the syringe chamber, either for priming or for injecting tissue. The injectate flows into an injection lumen in a shaft of the device, and from an injection orifice at the distal end of the shaft. The pressure source may be any source of energy such as a spring, compressed air, manual syringe, electric power, hydraulic, pneumatic pressure sources, etc.

Attached to the body, a needleless injector device of the invention can include an elongate shaft for placement within the urethra. The shaft includes an injection orifice located to inject fluid to internal tissue, e.g., through the urethra and into the prostate, when the device is installed.

The device includes a distal end and a proximal end. A distal end, including a shaft, generally is considered to include the portion of the device that is located internally within a patient's body during a treatment procedure. A distal end will typically include functional features that operate on tissue during use, such as an injection orifice, an injector head if used, one or more balloons or other form of positioning devices if used, and tissue tensioners if used.

A proximal end of a device includes a portion that remains external to the patient during use, (e.g., the body). A proximal end generally includes features that are not required to be internal during a treatment procedure such as a source of injectate and a source of pressure for the injectate; an eyepiece of an endoscope or other optical feature if included with the device; mechanical features such as a trigger or handle for holding or actuating a body or another feature at the distal end; adapters for attaching the proximal end to appurtenant equipment such as a source of power, a source of pressure, a source of fluid, or a source of vacuum, etc.

A shaft of an injector device may be an elongate component that in general extends from the proximal end to the distal end and includes features and componentry that allow for use and operation of distal end features by use and operation of proximal end features. A shaft may generally be of various constructions, as desired, e.g., may be of an integral construction that is not designed to be assembled and dis-assembled prior to, during, or after use; or may be of a multi-piece construction that includes multiple elongate shaft components or elements that fit together as an assembled whole for use in a surgical procedure and that can be assembled and dis-assembled before and after use if desired.

Either of a multiple-component or an integral construction-type shaft may be flexible or rigid and either type may include any of the features of devices described herein. Metal or polymeric materials may be useful for either type of shaft or for a component of either type of shaft. Materials that can be particularly useful for a rigid, multi-piece shaft may include rigid polymeric materials such as a rigid plastic or a rigid metal material. Specific examples include nitinol, polycarbonate, stainless steel, and the like. Materials useful for a flexible shaft or a flexible component of a multi-piece shaft can be relatively flexible polymeric materials such as polymeric materials known to be useful for catheter devices such as urethral catheters (e.g., Foley catheters). Specific examples of flexible polymeric materials include silicones, polyurethanes, rubbers, latex, and the like.

A single-component or "integral" shaft for an injector device is a shaft that is substantially or completely assembled at the time of manufacture of the device and that is not designed to be assembled or dis-assembled prior to or after use. The shaft may be flexible or rigid and may be prepared from metal or polymeric materials. A flexible integral shaft includes a flexible elongate component that extends from a proximal to a distal end of the injector device, and that defines or includes necessary functional elements such as injection orifices, lumens, etc., to operate the features at the distal end from the proximal end. These features of the shaft portion of the device are substantially permanent features of the device that are not designed to be removed from or dis-assembled into multiple components of a shaft.

According to certain embodiments an integral shaft can be a flexible shaft prepared from a flexible polymer, and can include lumens that connect distal end features to the proximal end of a device. The lumens can be flexible lumens defined by or embedded in the shaft or in a wall of the shaft. If necessary a lumen can be of sufficient strength to withstand elevated pressures such as in the case of an injection lumen that connects an injection orifice at a distal end to a pressurized supply of injectate fluid at a proximal end. Exemplary elevated pressures ("injection pressures") may be 2000 pounds per square inch or greater. An injection lumen may be of a flexible material (e.g., a metal or polymeric tube) that can withstand such an injection pressure, and may be prepared from exemplary materials capable of withstanding pressure of an injection, e.g., nitinol, stainless steel, reinforced (e.g., braided) polymer.

"Flexible shaft" refers to a shaft that is sufficiently pliable to allow bending and flexing that allow the shaft to be inserted through the meatus and to allow a portion of a distal end of the shaft to be guided into the urethra as can be done with a Foley catheter.

An integral shaft can be prepared with materials and methods similar to those used to prepare known urethral catheter devices such as a Foley catheter, but adapted to include a needleless injection mechanism and optionally other features as described herein. An integral shaft may include any one or more of: one or multiple injection orifices; moveable injection orifices; tissue tensioners; balloons for locating the device; an optical feature such as an endoscope or a flexible fiber optic cable; etc. Any one or more of these features can be located along a desired length of a device or at a specific location at a distal end of a device, along the integral shaft, and can be functionally connected to the proximal end by lumens or actuating mechanisms.

An integral shaft can be particularly useful with devices that include a flexible shaft and that contain a tissue tensioner or a device-locating feature such as one or more balloons at the distal end for locating the device during use. The use of a device-locating feature may advantageously eliminate the need for an optical feature such as an endoscope, allowing for injections to be carried out with blind vision methods. Particular devices of the invention may include an integral flexible shaft, injection orifices, one or more tissue tensioners, and other features of a urethral catheter such as one or more inflatable balloons at the distal end, and a drainage orifice at the tip and a drainage lumen leading from the bladder (when installed) to the proximal end of the device. Such devices, including a flexible shaft, a drainage lumen to drain urine from a bladder (e.g., as does a Foley catheter), and optional balloon, may be referred to as an "injection catheter" embodiments of the invention. In use, "injection catheter" embodiments may be inserted through the external orifice of the urethra (meatus) as with a Foley catheter, as opposed to being inserted through an external incision and a tissue path to the urethra as with rigid-shaft injector devices.

As opposed to an integral shaft, shafts referred to as "multiple-component" shafts may include two or more elongate pieces or components that fit together as an assembled whole and that can be dis-assembled prior to or after use. Typical components of a multiple-component shaft include an outer shaft or "sheath" in the form of an elongate rigid hollow sheath, and one or more additional inner shaft components that can be assembled together with the outer shaft to form a functional, assembled, multi-component shaft.

An outer shaft or "sheath" of a multiple-component shaft may be a basic sheath that is sized and shaped to be placed in the urethra while containing one or more inner shaft components. A sheath component of a multi-piece shaft may include just a hollow and rigid sheath, or may include a hollow and rigid sheath having functional features of a device such as one or more of a tissue tensioner, an injection lumen or injector head, a positioning component such as one or more balloons, and one or more lumens that connect a functional feature at the distal end of the sheath to the proximal end. An exemplary outer shaft can be a rigid (e.g., of metal or a rigid plastic) sleeve that can be inserted in a patient from an external incision, to define a passage from the external incision into the prostatic urethra. When inserted, one or more inner shaft components can be inserted into the outer shaft, as desired.

An inner shaft component of a multi-component shaft can fit within the outer shaft component or sheath and may include one or multiple functional features of a device such as one or more injection orifices, one or more lumens, one or more injector heads, or an optical feature such as a lens, open viewing channel, tissue tensioner, etc. An inner shaft that includes an injector head or an injection orifice may be specifically referred to as, e.g., an inner "injection shaft," and may include an injection orifice at a distal end connected through an injection lumen to a proximal end of the inner ("injection") shaft component. Optionally, an inner shaft component (or a feature thereof such as an injection orifice or an injector head) can be moveable within an outer shaft component or shaft generally, for any reason, such as to allow movement of an injector head or injection orifice during use.

Also optionally, as desired, embodiments of the invention may combine multiple device features into a single rigid shaft component. For example, a rigid shaft component may combine an outer sheath with an injection shaft, and may be sized and shaped to receive an endoscope. Alternately a rigid shaft component may combine an outer rigid sheath with an endoscope, and may be sized and shaped to receive an inner "injection shaft" that contains an injection lumen and injection orifice. As yet another alternative, the endoscope may also be combined with an outer shaft component and injection features into a single rigid shaft that is not designed to be assembled and disassembled.

Generally, any of the various shaft designs may be used with either blind vision methods or direct vision methods. An optical feature can be incorporated into any of a multiple-component, integral, rigid, or flexible shaft, using known materials and constructions, such as with an endoscope or any form of fiber optic device or other optical device. An eyepiece can be located at the proximal end of a device and one or more of an open vision channel, optical fiber, lens, multiple lenses, mirrors, refractive or reflective devices, or combination of these, can be used to create visual communication between the proximal end and a location at the distal end of the device. For a flexible shaft, for example, a flexible optical fiber can run from an eyepiece at the proximal end of the device to the distal end of the device at a location along the shaft. The optical fiber allows viewing of the distal end of the shaft, e.g., at a location to view an injection orifice.

With direct vision methods an optical feature such as an endoscope or optical fiber, etc., can be used to view internal tissue such as the internal urethra to facilitate placement of an injection orifice or multiple injection orifices as desired, e.g., within the prostatic urethra. Blind vision methods, on the other hand, can eliminate the need for an optical feature such as an endoscope and may instead rely on positioning of an injection orifice or orifices by use of other features such as the known dimensions of a device or positioning features at the distal end of the device, e.g., one or more of a distal or a proximal balloon, distance demarcations at the proximal end of the device, tissue tensioner, moveable orifice, which together can allow for blind delivery.

Any combination of shaft properties (e.g., rigid or flexible shaft) and other features described herein can be useful in injector devices, as desired. Certain specific features or combinations of features may be particularly useful with either rigid or flexible shaft designs. A rigid multi-component shaft may be particularly useful in combination with a direct vision feature and may optionally exclude the use of other types of positioning features such as one or more balloons at the distal end of the device. In addition, a rigid shaft may optionally not require the use of a tissue tensioner because a rigid shaft can be used to apply pressure between an injection orifice or injector head at a distal end of a device, and internal tissue. Still, a tissue tensioner may be desirable or useful as part of a device that includes a rigid shaft, e.g., those that include an injector head that places a small distance between an injection orifice and internal tissue at the site of injection (see below).

Certain integral, flexible shaft embodiments of devices may be useful as including a flexible shaft and can provide advantages such as patient comfort due to the flexible shaft, elimination of the need for an external incision to access the urethra (as is normally used with rigid shaft designs) and optionally the use of blind vision injection methods based on the use of positioning features such as balloons at the distal end of the device. These devices may include a flexible shaft that includes features for placing and fixing the distal end of the device to locate one or more injection orifices as desired, e.g., within the prostatic urethra (i.e., "positioning features"). Advantageously, the flexible shaft may be inserted through the external urethra orifice (meatus) (e.g., in the manner of insertion used for a Foley catheter) without requiring an external incision or a tissue path from the external incision to the urethra. The use of positioning features can avoid the need for an optical component for locating a distal end. Exemplary positioning features include one or combinations of: visible distance demarcations at the proximal end that can be used to gauge the location of a distal end, an injection orifice, or positioning feature (e.g., balloon) relative to the prostatic urethra or bladder; known dimensions of the device; one or more balloons; tissue tensioners; or other positioning features at the distal end of the shaft. Also useful to avoid the need for an optical feature are moveable features such as a moveable injection orifice, to allow movement of an injection orifice along a length of the device after the device may be to some degree fixed internally, e.g., within the urethra.

According to devices of the invention, one or multiple injection orifices are located at the distal end of the device at a location or locations along the shaft that place the orifice or orifices at a desired location internal to the patient upon installation, e.g., within the urethra proximal to the prostate (i.e., the prostatic urethra). The orifice or orifices are in fluid communication (e.g., through an injection lumen) with a fluid source that can be pressurized to eject fluid from the injection orifice and into a tissue, e.g., through the urethra and into the prostate. The injection lumen that connects the injection orifice to the proximal end of the device (and the fluid source) extends along a length of the shaft and is of a material that can withstand a pressure produced during ejection. Multiple orifices may be arranged at different locations around the perimeter of the shaft, or may be located at different lengths along the shaft, or both. Optionally, an orifice or orifices may be moveable relative to the shaft, either rotationally around a longitudinal axis of the shaft or lengthwise along a length of the shaft. Each of multiple orifices may be connected separately to the pressurized fluid source to allow fluid to be separately ejected from each orifice, if desired; or multiple orifices may be connected together to a fluid source to allow ejection from multiple orifices at once.

An injection orifice may have any useful size (e.g., length and diameter) for producing desired properties of an injection such as desired exit velocity, injectate volume, injectate dispersion (e.g., size and shape of a cloud of injected particles), etc. Examples of useful orifice diameters may be in the range from about 0.001 to 0.05 inches, depending on factors such as the desired injection parameters and the type and size (e.g., depth) of tissue being injected. The injection orifice may be larger or smaller than the injection lumen adjacent to the injection orifice, if desired, to affect the exit velocity of the injectate at the injection orifice. Examples of useful orifice shapes may include features such as a venturi, a continuous uniform diameter along the length of an orifice, a funnel-shape, etc. As is known, a relatively smaller diameter orifice may produce an injection depth of greater penetration into tissue compared to a larger diameter orifice (with identical injection pressure).

According to particular embodiments, an orifice may be included at a location of a shaft as part of a larger structure that can be referred to as an "injector head." An injector head can be considered to be a component of a needleless injector device that includes one or multiple injection orifices and one or more functional surfaces, in various arrangements. Examples of functional surfaces include a surface that contacts internal tissue (e.g., urethral tissue) during an injection step, and a surface that includes an injection orifice, the two of which may or may not be the same. Any one or more surface of an injector head may be flat, arcuate, curved, etc. A surface that contacts internal tissue during injection may include one or multiple injection orifices, or other features (such as one or more vacuum orifices as described in more detail below), and may be shaped and sized to produce a desired effect on the tissue such as to place tension on the tissue. Optionally, an injector head may be moveable relative to the shaft either rotationally around the longitudinal axis of the shaft or lengthwise along a length of the shaft.

Also optionally, embodiments of injector heads may include a first surface that contacts internal tissue during injection and a second surface that includes one or more injection orifices, the second surface being displaced from the first surface by a small distance and being located on the injector head to not contact internal tissue during injection. According to this embodiment an injector head is designed to place an injection orifice at a desired distance away from internal tissue during injection for the purpose of affecting and controlling features of the injectate upon injection, such as the degree to which injectate particles become dispersed throughout injected tissue (e.g., prostate tissue) and the distance of travel (penetration) of dispersed injectate particles. As an example, an injector head may include a recessed flat surface that includes one or multiple injection orifices, and a second surface that surrounds the first surface, the second surface being proximal to the first surface but displaced a small distance above the first surface. The distance (if any) between an injection orifice and tissue into which injectate is delivered can affect the penetration distance of the injectate—a relatively smaller distance between tissue and an orifice will result in increased penetration of an injection compared to a similar injection from a greater distance.

The injector head can be of a material such as a metal that is useful to provide an injection orifice capable of delivering a high-pressure injection as described herein. The injector head can be stationary or may be moveable along the length of the shaft of the injector device. Alternately or in addition the injector head may be moveable in a rotational direction around the longitudinal axis of the shaft of the needleless injector device.

A pressurized fluid source is connected to an injection orifice by an injection lumen. To accommodate an operating pressure necessary to inject fluid through tissue (e.g., to transverse the urethra and travel a distance into the prostate), the injection lumen must be formed of a material that also withstands the injection pressure. Depending on the overall design and features of a device, an injection lumen may be either flexible or rigid, and may be formed of rigid metal, a flexible metal, a flexible polymer, a reinforced polymer composite, etc., any of which will withstand a useful injection pressure.

The pressurized fluid source can include a source of fluid and a source of pressure ("pressure source"). The pressure source may be mechanical (such as a spring), pneumatic, hydraulic, electric, etc., as will be understood. The pressure source may be mechanically or electronically controlled. The pressure source can cause a fluid contained in a fixed- or variable-volume chamber to be pressurized to a transient pressure, at the injection orifice, that is sufficiently high to allow the fluid to be ejected from the injection orifice with sufficient force to penetrate internal tissue such as to traverse the urethra and to then penetrate a desired distance into the prostate.

Additional potential features of injector devices of the invention, for optional use in combination with other features described herein, include inflatable balloons located at the distal end of the shaft of the injection catheter, e.g., as "positioning features." An injector device may include one or multiple balloons at a distal end, allowing the device to be placed and fixed at a desired position during use. A balloon for locating the injector device can be particularly useful in combination with a device that does not include any optical feature such as an endoscope to directly view the operation of distal features of the device such as an injection orifice. Placement of a balloon at the distal end of the device, at a known distance from an injection orifice, can facilitate proper placement of the injection orifice, such as within the prostatic urethra, based on the positioning of the balloon.

An example of a balloon that allows a surgeon to locate an injector device as desired is a balloon that can be placed within the bladder or at the bladder neck when the device is installed. The balloon may be of a type used in a Foley catheter but adapted to function at the end of rigid or flexible shaft of a needleless injector device as described herein. The balloon can be useful to fix the overall location of the device during use, i.e., to place the shaft of the device at a desired location to cause one or more injection orifices to be located as desired, e.g., within the prostatic urethra. The balloon can be located on the shaft at a location distal to the injector head. When the device is installed, the balloon can be in the bladder or bladder neck, and can properly locate the device during treatment, and can also seal the bladder neck from the prostatic urethra.

Another optional feature of an injector device of the invention, for optional use in combination with other features described herein, is an inflatable "proximal" balloon located at the distal end of the shaft of the device but on the proximal side of an injection orifice or orifices. A proximal balloon can be designed to also locate and fix the location of the device during treatment. Additionally, a proximal balloon can function to seal the proximal (lower) end of the urethra. With a balloon sealing the distal end of the urethra (e.g., at the bladder or bladder neck) and a proximal balloon sealing the proximal end of the urethra, the balloons can together define a "zone of treatment" within the urethra that extends approximately the length of the prostate or the length of a desired portion of the prostate that will be treated. The balloons seal the ends of the prostate, which advantageously prevents injectate from passing outside of the zone of treatment within the urethra.

Another feature of a needleless injector device for optional use in combination with other features described herein, is a tissue tensioner located at a distal end of the device. A tissue tensioner is located at the shaft, somewhat near to an injection orifice, e.g., to be within the prostatic urethra and near the injection orifice when the device is installed. A tissue tensioner can be a mechanism capable of contacting tissue, e.g., urethral tissue, to hold a desired portion of the tissue in place relative to an injection orifice, and to optionally produce a tension or strain on the tissue in a manner that can affect the manner in which injectate penetrates the tissue and becomes distributed in the tissue upon injection. While a tissue tensioner can be used in combination with any of the other features described herein, including rigid shaft embodiments of devices, a tissue tensioner may be particularly useful when used with a device that includes a flexible shaft. The tissue tensioner can facilitate a good result upon injection of fluid through the urethra by ensuring that the internal urethral tissue is fixed and includes a desired amount of tension for receiving an injection.

Depending on the configuration of an injection orifice at a shaft of a device, or at an injector head, a tissue tensioner can be used to place a desired portion of tissue in direct contact with an injection orifice, i.e., a surface that contains an injection orifice. Alternately, a tissue tensioner can place a desired portion of tissue at a desired distance away from an injection orifice, e.g., in the instance of an injector head that includes two surfaces with a recessed surface including an injection orifice. The distance, if any, between an injection orifice and tissue, at injection, can be selected to affect properties of the injection, e.g., to affect the distance an injectate penetrates into tissue, the size of droplets, and the pattern over which droplets of injectate are dispersed throughout tissue when injected. Other factors can also be adjusted to affect properties of the injection such as pressure and volume of injectate, size and shape of the injection orifice, etc.

Examples of types of tissue tensioners include inflatable balloons located at a shaft near an injection orifice, and mechanically extendable or retractable components such as paddles, protrusions, levers, metal cages, and the like, any of which can be extended from a shaft of an injector device to place pressure on internal tissue, e.g., on urethral tissue within the prostatic urethra.

A balloon or a mechanically extendable or retractable tissue tensioner can be inflated or extended at a location that is approximately at a length along a shaft that is near an injection orifice. When used within a urethra, the tissue tensioner can push urethral tissue away from the shaft in a manner that causes urethral tissue and an injection orifice or injector head to contact each other. This can be done, for example, by a balloon expanding from an opposite side of a shaft relative to an injection orifice, to place pressure on urethral tissue located opposite from an injection orifice and to cause the injection orifice or a nearby surface to meet, optionally to produce pressure, strain, or tension on the urethral tissue opposite of the balloon. A mechanical tensioner may be extended from a shaft of a device by use of an actuating mechanism such as a mechanical connection between the tensioner and the proximal end of a device.

Another embodiment of tissue tensioner can be a pressure differential produced by vacuum. Vacuum can be created near an injection orifice, for example, in a manner that can pull urethral tissue and an injection orifice or injector head into contact, and optionally place a tension or strain on the tissue of the urethra at the location that will receive injectate. This can be done, for example, by including vacuum orifices near an injection orifice, e.g., along a shaft or at an injector head. The vacuum orifice can pull vacuum causing the shaft or injector head to contact the internal tissue of the urethra near the injection orifice, causing the urethral tissue to contact the catheter shaft or injector head. The vacuum orifice can be in fluid communication with the proximal end of the device through a lumen extending along the shaft, e.g., a vacuum lumen.

Embodiments of injector devices of the invention, in addition to any one or more of the above-described features, in any combination, may include safety features that prevent inadvertent or improper actuation of a device or inadvertent or improper ejection of fluid from a device. Examples of a safety feature may be any feature that prevents actuation of an injection mechanism if a device is not properly installed and properly located, internally, with the device and injectate in a ready position to make a desired injection.

One example of a safety mechanism that would prevent actuation of an injection mechanism if injectate fluid is not present at an injection orifice or an injection lumen may be an air detector located at the injection orifice or injection lumen. This mechanism would directly determine whether an injectate fluid is present in an injection lumen and at an injection orifice. A fluid may be detected by known techniques, such as by detecting microscopic bubbles in a fluid using ultrasound or optical methods. If fluid is not present the device would be programmed to prevent actuation of the injection mechanism.

Another type of safety mechanism that would prevent actuation of an injection mechanism, if injectate is not present at an injection orifice or an injection lumen, is a priming mechanism to ensure that a fluid is located properly within an injection lumen upon manufacture, sale, or during use of a device. This type of a safety feature does not directly determine whether an injectate fluid is present in an injection lumen and injection orifice, but provides a level of assurance that injectate is properly located within the device for injection by allowing for a priming step. A priming mechanism could be used in combination with an air sensor described above.

Optionally, embodiments of the invention can include a device sold in a pre-primed condition (optionally in a sterilized package), with a fluid contained within the injection lumen. The fluid may be, e.g., an anesthetic, saline, an antibiotic, ethanol, or another biologic agent, depending, for example, on the intended use of the injector device. The injector device can be pre-primed, meaning that the injector device is in a primed condition as supplied to a surgeon. The pre-primed injector device can be primed during manufacture and prior to distribution and sale, e.g., a device can be packaged and sold to a user in a primed condition. When a surgeon or assistant removes the device from a sterilized package, the device is already primed and may include a desired amount and type of injectate fluid within the injection lumen and, optionally, a reservoir or other chamber at the proximal end. The surgeon may use the device without having to prepare the device by, e.g., adding injectate fluid to the device or priming the device to place injectate fluid into the injection lumen. Optionally the pre-primed device may be disposable.

In general, a priming mechanism can be any mechanism that is useful to place fluid in an injection lumen prior to a high-pressure injection into tissue. During normal use, prior to making an injection, fluid may be contained by a fluid chamber at a proximal end of the injector, which is in fluid communication with the injection lumen and injection orifice. To prime the device, injectate is caused to flow at relatively low pressure from the fluid chamber into the injection lumen, to fill the injection lumen until injectate flows (e.g., slowly) from the injection orifice. Low pressure flow may be produced, e.g., by applying pressure to the fluid in the fluid chamber, by use of a pressure source as described herein. Low pressure flow is a rate of flow that would not allow injectate flowing from the injection orifice to penetrate tissue, and typically is greatly below a rate of flow that would allow tissue penetration.

Embodiments of injector devices of the invention, in addition to any one or more of the above-described features, in any combination, may include still further features that add convenience or efficiency to a needleless injector device. Examples include specific trigger mechanisms, actuating systems, or control systems (e.g., electronic and computerized control systems) that allow for multiple injections, and methods and features for controlling or programming volumes, depths, timing, order, positioning, or other features of one or multiple injections.

In particular embodiments, a trigger and control system could include a series of multiple positions that produce multiple actuations such as engagement of a tissue tensioner, actuation of an injection mechanism, movement of an injector head, etc. For example, a first trigger position may cause engagement of a tissue tensioner and a second trigger position may cause the injector to be actuated to inject fluid.

Any individual component, or an entire device, could be disposable or reusable. As an example, a disposable or reusable optical feature such as an endoscope could be incorporated into a portion or component of a device that is either disposable or reusable. Additionally or alternately, a device could have a reusable pressure source (e.g., cartridge of pressurized gas), a replaceable fluid reservoir, a disposable injector head portion, or may be entirely disposable.

In another particular embodiment, a device could be designed to inject multiple volumes of injectate at different tissue locations. Accordingly, the injections may be made between steps of relocating an injection orifice, wherein the injection orifice may optionally be moveable relative to the shaft. The multiple volumes of injectate could be pre-loaded into individual, e.g., replaceable, vials of a predetermined volume as desired for a single or multiple injections, i.e., a single vial may include a single dose (volume) or multiple doses (volumes) of injectate. With the use of a replaceable vial, the device could be used to inject one or multiple doses of injectate using the entire volume from one vial. The replaceable vial could then be removed from the injector device and replaced with a full vial, and the volume of the full vial could be injected in one or more injections. This could be repeated for as many injections as desired. In alternate embodiments, the device may have a connection at the proximal end for connecting the device to a source of injectate fluid (e.g., a "hopper") from which multiple injections of desired volumes could be sourced without the need for loading or reloading individual vials.

With any of the above features of injector devices, a device could include an electronic process control system that can be programmed to deliver injections having various locations, volumes, and other injection properties such as depth and degree (e.g., shape and distance) of dispersion and size of particles of injectate.

The attached figures illustrate various features of injector devices as described and for use in treating a prostate.

FIG. 1 illustrates injection catheter 10, which includes three stationary injector heads 2 along a portion of shaft 16. Each of injector heads 2 includes injection orifice 4 at the center of injection head 2 and vacuum orifices 6 surrounding each injection orifice. Distal end balloon 8 is located at tip 14 of device 10 and can be used to fix and locate device 10 during use by being inflated within the bladder or bladder neck. Proximal balloon 12 can be used to fix and locate device 10 during use by being inflated within the urethra, e.g., at the proximal end of the prostatic urethra. Tip 14 includes drainage apertures 18 connected to a proximal end of the device (not shown) by drainage lumen 20. Each of injection orifices 4, vacuum orifices 6, and distal and proximal balloons 8 and 12, are in fluid communication with a distal end of the device, by lumens 22, located for illustration within the sidewalls of shaft 16.

FIG. 2 illustrates a portion of another embodiment of an injector device. Device 30 includes shaft 32; a tissue tensioner in the form of expandable metal cage 34; and moveable injector head 38, which can be moved along a length of shaft 32 within slot 36. Injector head 38 connects to a proximal end of device 30 through moveable injection shaft 31, which extends within a hollow center of shaft 32. Injector head 38 includes a ring of eight vacuum orifices 42 surrounding a central injection orifice 44. Actuating mechanism 40 is located within a lumen of a wall of shaft 32, and can be actuated to cause extension and retraction of expandable metal cage 34.

Figure 2A:
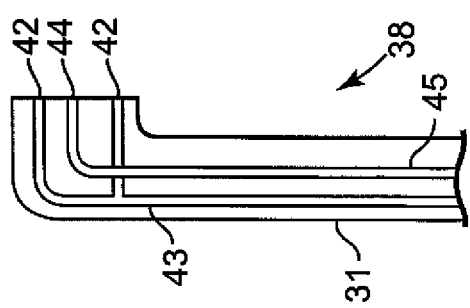

FIG. 2a illustrates a cut-away side view of injector head 38, including vacuum orifices 42 and injection orifice 44. FIG. 2a specifically illustrates vacuum lumens 43 and injection lumen 45, which are in fluid communication with a proximal end of device 30 through moveable injection shaft 31.

FIG. 3 illustrates a portion of another embodiment of an injector device. Device 50 includes shaft 52; a tissue tensioner in the form of expandable balloon 54; and moveable injector head 58, which can be moved along a length of shaft 52 within slot 56. Injector head 58 includes a ring of vacuum orifices 66 included on a surface 62. Recessed surface 64 includes injection orifices 68 (three orifices as illustrated). Lumen 60 is located within a wall of shaft 52, and is in fluid communication with a proximal end (not shown) of device 50, to allow inflation of balloon 54. Injector head 58 connects to a proximal end of device 50 through moveable injection shaft 51, which extends within a hollow center of outer shaft 52.

Figure 3A:
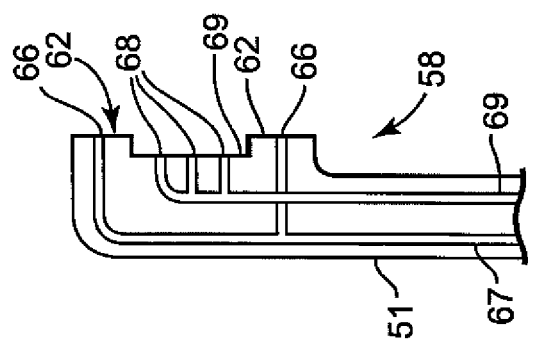

FIG. 3a illustrates a cut-away side view of injector head 58, including vacuum orifices 66, injection orifices 68, surface 62, and recessed surface 64. FIG. 3a specifically illustrates vacuum lumens 67 and injection lumens 69, which are in fluid communication with a proximal end of device 50 through moveable injection shaft 51.

Figure 4C:
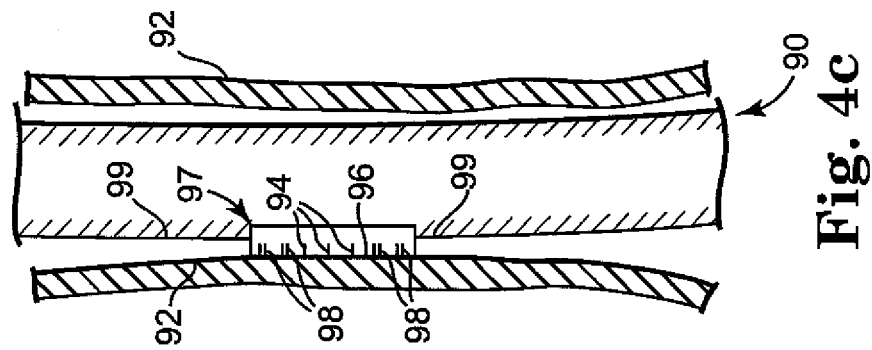
FIGS. 4a, 4b, 4c, and 4d illustrate exemplary components of a shaft of an injector device, including tissue tensioning features.
Figure 4B:
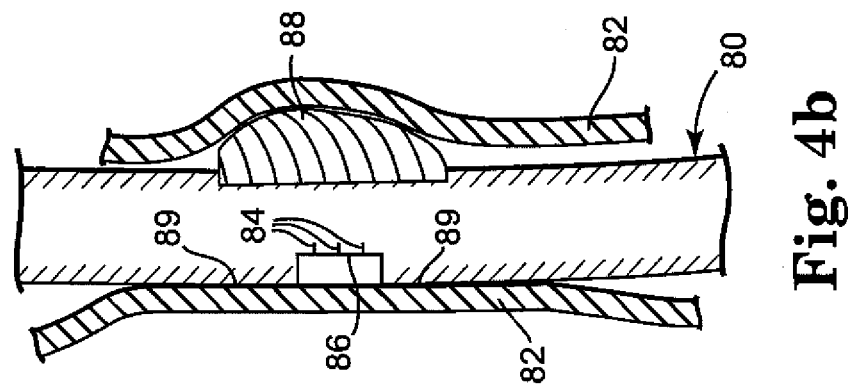
Figure 4A:
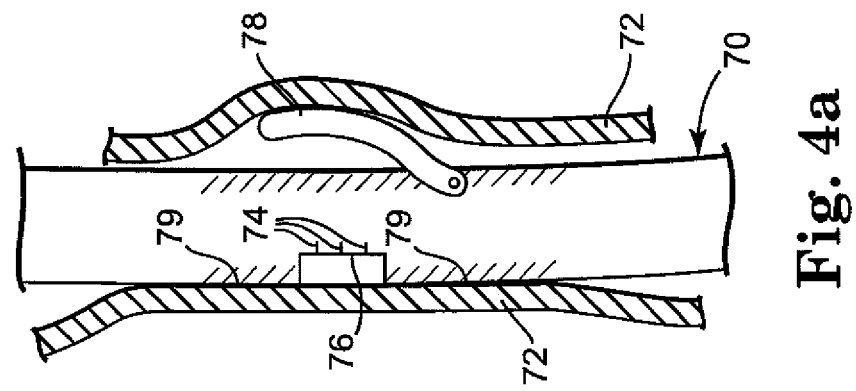

FIGS. 4a, 4b, 4c, and 4d, each illustrate various alternate embodiments of tissue tensioners, as could be incorporated into any one of the injector devices illustrated or described herein. FIG. 4a shows device shaft 70 inside of urethral tissue 72. Injection orifices 74 are included at surface 76, which is recessed from outer surface 79 of shaft 70, proximal to injection orifices 74. Tensioner 78 is extendable and retractable by use of an actuating mechanism (not shown) within the injector device. Tensioner 78 is shown in an extended state whereby tensioner 78 contacts tissue 72 on a side of the urethra that is opposite of the tissue that will be contacted by fluid ejected from injection orifices 74. Orifices 74 and surface 76 are not in direct contact with urethral tissue but are separated by a small distance defined by the distance that surface 76 is recessed from surface 79. By contacting and pushing tissue opposite of orifices 74, urethral tissue 72 and surface 79 are placed into contact. Tissue 72 near surface 79 is stretched or tensioned to a desired extent, to affect or control the manner in which an injectate dispersed at high pressure from orifices 74 will penetrate urethral tissue 72 and become dispensed in prostate tissue (not shown).

FIG. 4b illustrates another embodiment of a tissue tensioner in the form of an inflatable balloon located near an injection orifice. FIG. 4b shows shaft 80 inside of urethral tissue 82. Injection orifices 84 are included at surface 86, which is recessed from the outer surface 89 of shaft 80, proximal to orifices 84. Tensioner 88 is a balloon that can be inflated and deflated through an inflation lumen (not shown) within the injector device and in fluid communication with a proximal end of the device (also not shown). Tensioner 88 is shown in an inflated state whereby tensioner 88 contacts tissue 82 on a side of the urethra that is opposite of the tissue that will be contacted by fluid ejected from injection orifices 84. Orifices 84 and surface 86 are not in direct contact with urethral tissue 82 but are separated by a distance defined by the distance that surface 86 is recessed from surface 89. By contacting and pushing tissue opposite of orifices 84, urethral tissue 82 and surface 89 are placed into contact. Tissue 82 that is near surface 89 is stretched or tensioned to a desired extent to affect or control the manner in which an injectate (dispersed from orifices 84) will penetrate urethral tissue 82 and become dispensed in prostate tissue (not shown).

FIG. 4c illustrates another embodiment of a tissue tensioner in the form of vacuum orifices located near an injection orifice of an injection catheter. FIG. 4c shows injection catheter shaft 90 inside of urethral tissue 92. Injection orifices 94 (three illustrated) are included at surface 96, which is part of an injector head 97 that extends from the outer surface 99 of shaft 90, proximal to orifices 94. Tensioner 98 is in the form of multiple (four as illustrated) vacuum orifices located at surface 96 of injector head 97, near orifices 94. Vacuum orifices 98 can create a vacuum force at injector head 97, near orifices 94, through a vacuum lumen (not shown) within the device and in fluid communication with a proximal end of the device. Vacuum orifices 98 can create a pressure differential that causes tissue of urethra 92 to contact injector head 97, as shown, in a manner that will place urethral tissue 92 in direct contact with injector head 97 and injection orifices 94.

Figure 4D:
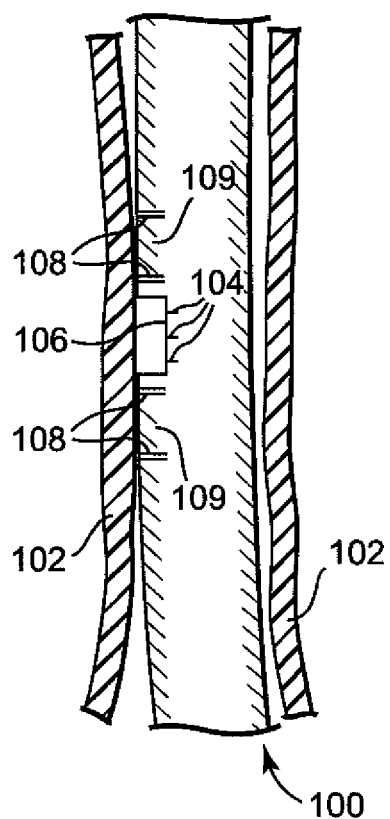

FIG. 4d illustrates another embodiment of a tissue tensioner in the form of vacuum orifices located near an injection orifice. FIG. 4d shows shaft 100 inside of urethral tissue 102. Injection orifices 104 are included at recessed surface 106, which is recessed from the outer surface 109 of shaft 100, proximal to orifices 104. Tensioner 108 is in the form of multiple (four as illustrated) vacuum orifices 108 located within shaft 100, near orifices 104. Vacuum orifices 108 can create a vacuum force at surface 109 of shaft 100, near orifices 104, through one or more vacuum lumens (not shown) within shaft 100 and in fluid communication with a proximal end (not shown) of the device. Injection orifices 104 and surface 106 are not in direct contact with urethral tissue 102, but are separated by a distance defined by the distance that surface 106 is recessed from surface 109. Vacuum orifices 108 can create a pressure differential that causes tissue of urethra 102 to contact surface 109 of urethral shaft 100.

Figure 5:
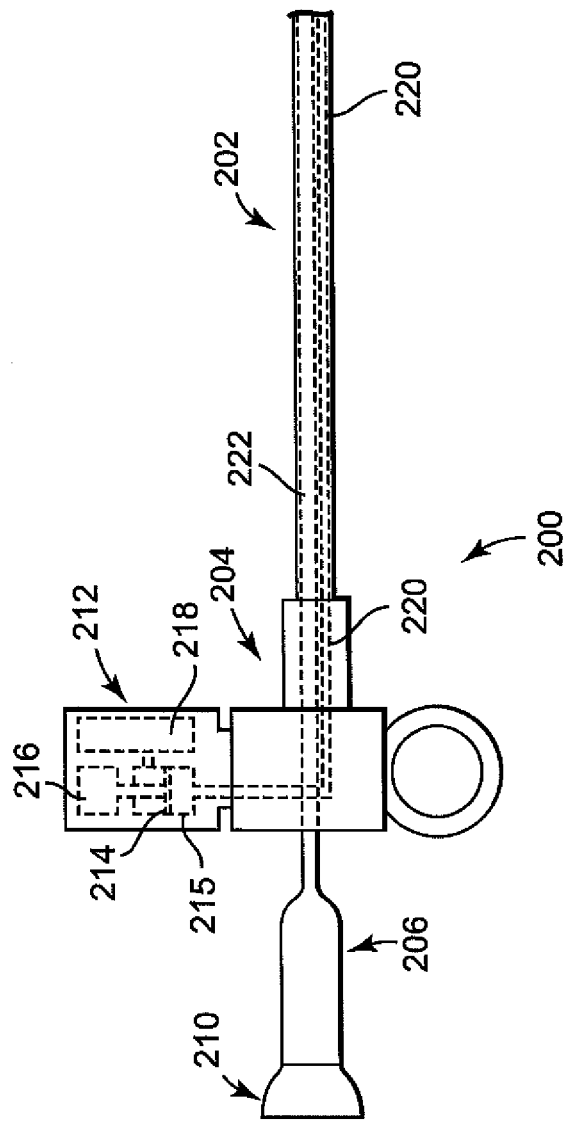
FIGS. 5, 5a, and 5b, illustrate exemplary components of an injector device.
Figure 5A:
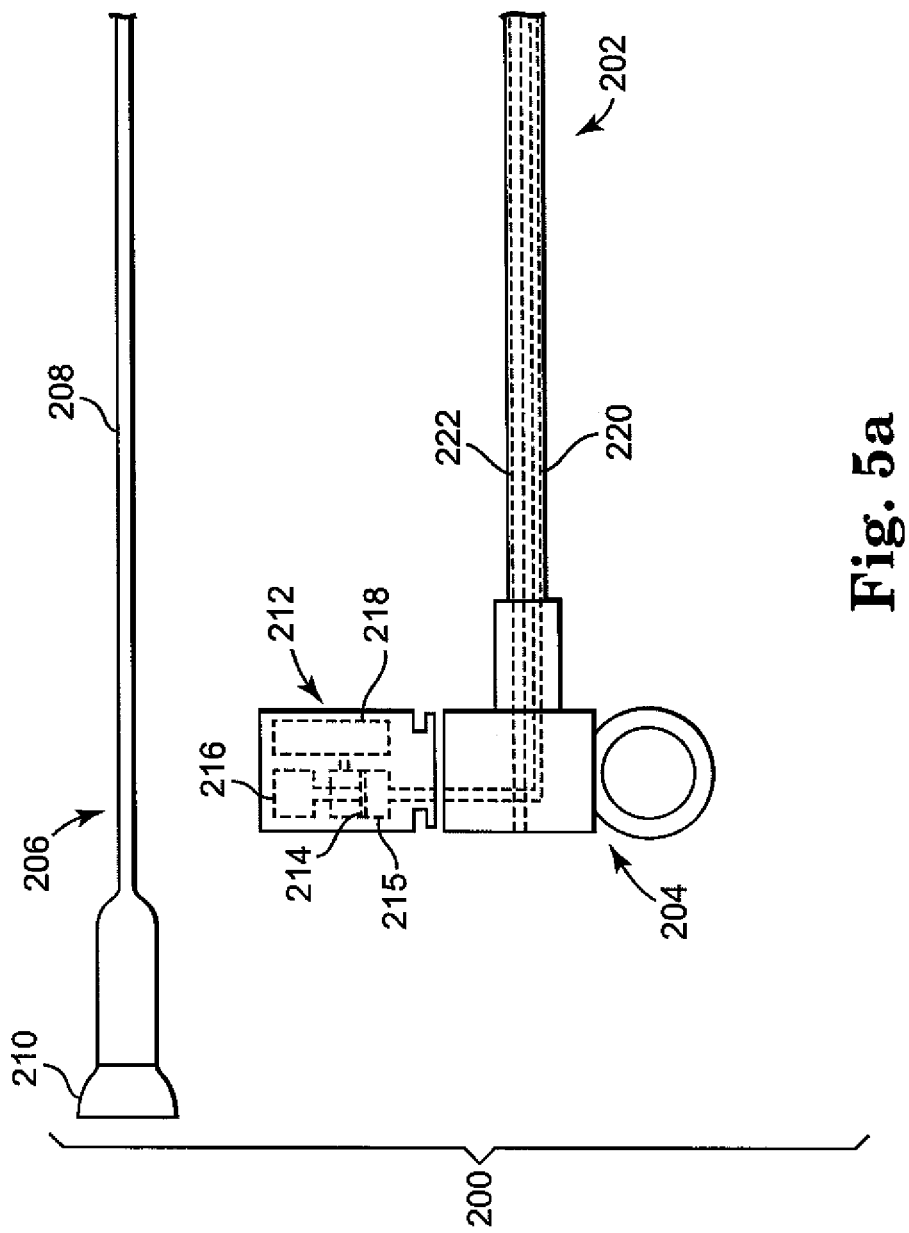
Figure 5B:
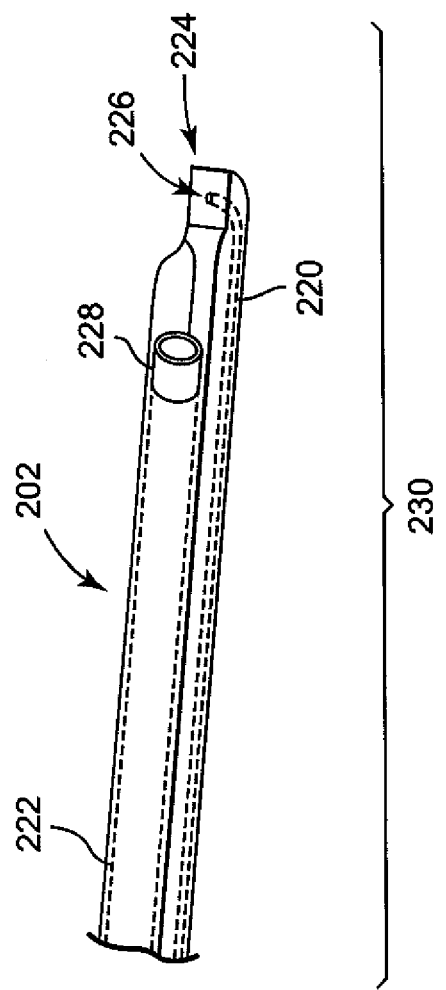

FIGS. 5, 5a, and 5b illustrate features of an embodiment of a device of the invention that includes a multi-component, rigid shaft. FIG. 5 shows the device in an assembled condition and FIG. 5a shows the device in an unassembled condition. Device 200 includes a rigid shaft 202, main body 204, optional scope 206 (illustrated to be removable), and power source 212. Power source 212, illustrated to be removable, includes features for providing injectate fluid and pressure to inject the fluid, e.g., a permanent or removable supply of injectate fluid in fixed-volume reservoir 218; a pressurizing mechanism (e.g., a plunger, bellows, syringe, etc.) 214 within a variable-volume chamber 215, and; a pressure source 216 for supplying pressure to pressurizing mechanism 214, which may be pneumatic, hydraulic, mechanical (e.g., a spring), electric, pressurized gas such as a carbon dioxide cartridge, an external source of pressurized gas or fluid, etc. Also included in power supply 212 but not specifically shown in FIGS. 5, 5a, and 5b, are mechanisms such as valving and tubing, etc., to allow reservoir 218, pressurizing mechanism 214, and pressure source 216, to work together to pressurize a fluid for injection through injection lumen 220.

Scope 206 includes scope shaft 208 and eye-piece 210. Scope 206 may be a commercially available rigid endoscope such as a cystoscope or laparoscope, for example. Suitable cystoscopes are available, for example, from ACMI (Classic and Elite models), Storz, Wolf and Olympus.

Main body 204 includes a port designed to mate with a power source 212, which can deliver a pressurized fluid injectate to main body 204. Shaft 202 includes injector lumen 220 and optical lumen 222. Injector lumen 220 aligns with a lumen of power source 212 such that pressurized injectate flows from power source 212 through injector lumen 220 and to an injection orifice at a distal end (not shown) of shaft 202.

Rigid shaft 202 includes optical lumen 222 to contain shaft 208 of scope 206, when the device is in an assembled condition. Rigid shaft 202 can be of a rigid material such as a metal and includes orifices or an injector head (not shown) at the distal end for injecting an injectate fluid. When optical scope 206 is placed within optical lumen 222 of shaft 202, scope 206 allows viewing of internal tissue for performing an injection.

Referring to FIG. 5b, a distal end 230 of device 200 is illustrated. Shaft 202 includes injection head 224, at the far distal end. Injection head 224 includes injection orifice 226 in fluid communication with a proximal end of device 200 through injection lumen 220. Distal end 228 of endoscope 206 is illustrated as inserted inside of optical lumen 222, and is illustrated to be removable. During use, the surgeon can view the area above injection head 224 and injection orifice 226 by viewing through eyepiece 210 of endoscope 206.

Device 200 can include one or more other functional features described herein but not specifically illustrated in FIG. 5, 5a, or 5b. For example, rigid shaft 202 can include a tissue tensioner, one or multiple balloons, or a tensioner and one or more balloons, each connected through lumens to a proximal end of the device. Alternately, injection head 224 may include a tissue tensioner, e.g., in the form of vacuum orifices.

Figure 6:
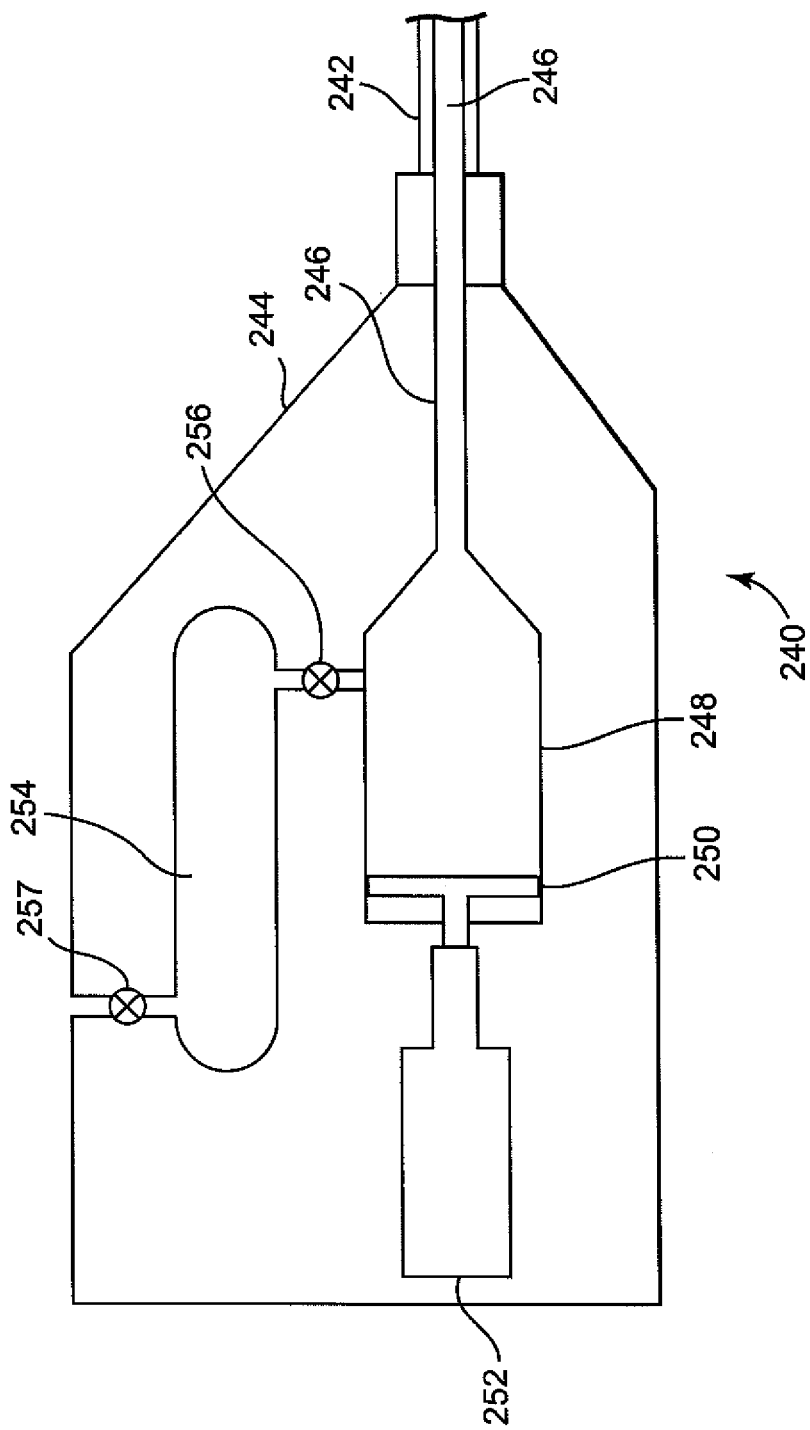
FIG. 6 illustrates exemplary components of a body of an injector device.

An embodiment of exemplary details of a body of a needleless injector device is shown in FIG. 6. FIG. 6 shows body 240 of a needleless injector device. An outer shaft 242 (rigid or flexible) extends from an end of body 240 to a distal end (not shown). Injection lumen 246 is defined by or contained by shaft 242 and is in fluid communication with variable-volume chamber 248. A pressurizing mechanism 250 (e.g., plunger) partially defines the volume of chamber 248 that is for containing injectable fluid and pressurizing the fluid. Pressure source 252 works with pressurizing mechanism 250 to move mechanism 250 to adjust the size of chamber 248 or to pressurize a fluid contained in chamber 248. Reservoir 254 can contain fluid injectate that can be caused to flow through valve 256 into chamber 248. Reservoir 254 may be permanent or may be removable from body 240.

Body 240 includes features of the invention useful to prime injection lumen 246 prior to use of the needleless injector device for delivery of injectate. For a priming operation, as will be appreciated, chamber 248 and injection lumen 246 may start partially or completely empty of injection fluid, and may contain a gas (e.g., air). According to the illustrated embodiment of body 240, to begin priming lumen 246 an amount of injection fluid is passed from reservoir 254 through valve 256, e.g., an amount to allow for lumen 246 to be filled (primed) and to still have sufficient injectate fluid remaining in chamber 248 for one or more dosage volumes to be injected from the needleless injector device. For example, fluid can be drawn from a filled reservoir 254 by opening valves 256 and 257, and drawing back piston 250 to increase volume within chamber 248. After placing fluid in chamber 248, to prime lumen 246, valve 256 is closed and pressure source 252 is actuated to cause plunger 250 to move forward and reduce the volume of fluid within chamber 248, i.e., forcing fluid into lumen 246. When lumen 246 is full, e.g., as shown by injectate fluid flowing from an injection orifice (not shown) at the distal end of shaft 242, priming is complete. After priming, an injection of injectate fluid can be delivered by again actuating supply 252 to cause plunger 250 to move further, this time to pressurize the remaining volume of fluid within chamber 248 and deliver a desired dosage of the fluid through injection lumen 246 for high pressure injection into tissue. The desired dosage may be all or only a portion of the fluid remaining in chamber 248 following priming.

The invention also provides a method of delivering fluid to tissue of the lower urinary tract, e.g., prostate tissue, including the steps of: providing a pressurized fluid source and a needleless injector device substantially as described above; inserting the needleless injector device into the patient; navigating the device until an injection orifice at a distal end of the device is positioned at a desired injection site; and actuating the device to inject fluid into tissue such as the urethra or prostate. By using a high-pressure needleless injection system, as opposed to a needle, the invention reduces trauma as compared to needle-based systems. Further, the injectate can advantageously be dispersed throughout a tissue instead of pooling. In addition, the high-pressure needleless injection system can reduce other undesired effects that occur by injection using a needle such as the need for overdosing, and the amount of injectate required is reduced.

Exemplary methods that can be performed using devices described herein include methods that relate to treating diseased prostate tissue. One form of treatment regimen includes the steps of chemically ablating prostate tissue sufficiently to elicit a reparative process in the absence of further treatment. The size of the prostate is reduced relative to the size prior to treatment. The treatment regimen is suitable for treatment of prostate tissue diseases including BPH and prostatic carcinoma.

Figure 7:
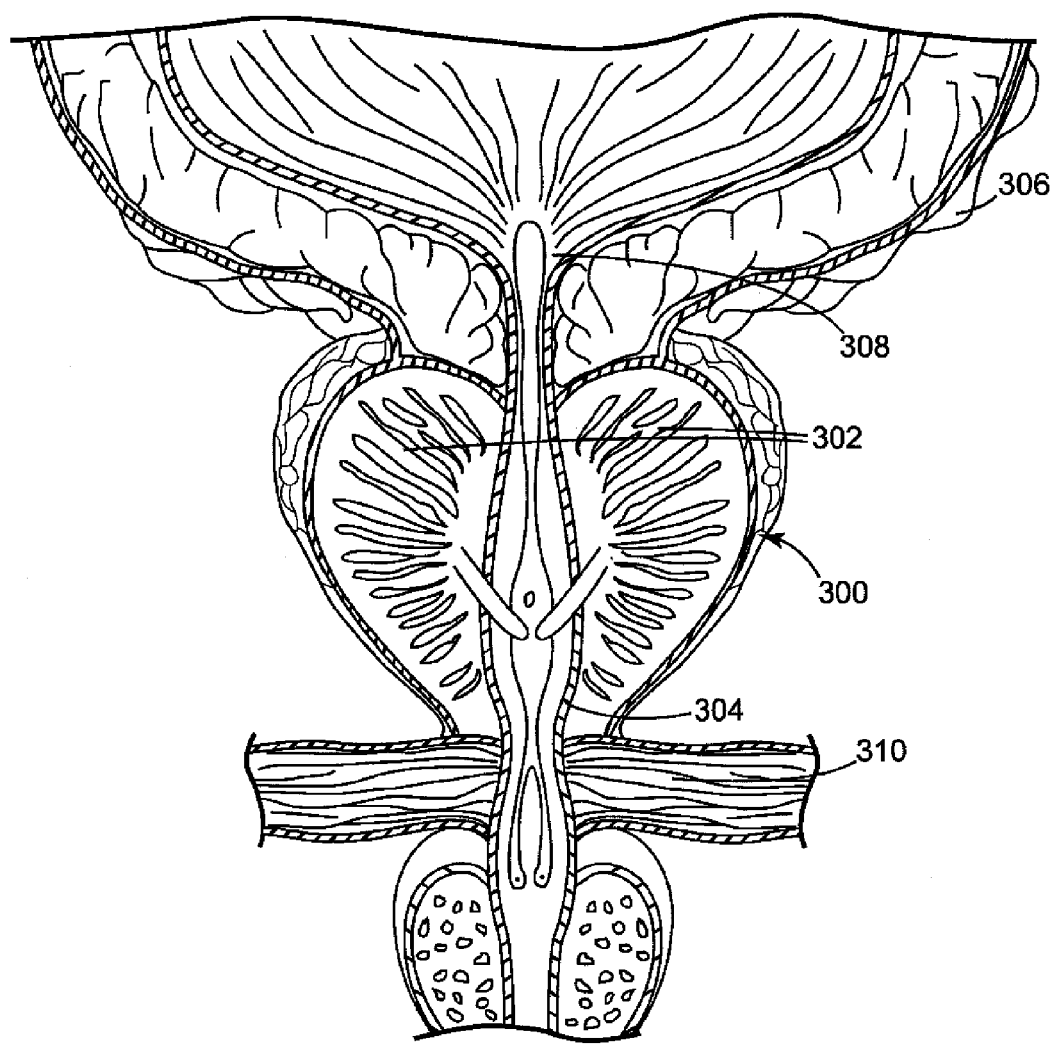
FIG. 7 illustrates a portion of anatomy of the lower urinary tract.

FIG. 7 shows the anatomical position of prostate 300 (including lateral lobes 302) surrounding urethra 304, and adjacent tissue including seminal vesicles 306, bladder neck 308, and pelvic tissues including sphincter muscles 310. Chemical ablation may be achieved, for example, by direct transurethral injection of a chemoablation fluid into a patient's prostate. The terms "ablate," "ablation," and "ablating," of tissue means causing a reduction in tissue mass. One suitable manner of ablating tissue is by causing a decrease in the number of tissue cells. The phrase "chemical ablation" includes processes whereby tissue mass is reduced by action of a chemical or biological agent on the tissue, such as ethanol. One suitable procedure for chemically ablating prostate tissue in accordance with the treatment regimen is by injection of ethanol (absolute alcohol) into the prostate to be treated. The ablating action of ethanol is due to several processes, including dehydration of cells, coagulation of proteins, and thrombosis of vessels that feed the tissue.

According to needleless procedures of the invention, an injectate such as ethanol can be injected into prostate tissue transurethrally in a manner that disperses particles or droplets of the injectate throughout prostate tissue. The manner in which the injectate enters and becomes dispersed throughout the prostate can be characterized by various controllable factors such as one or more of the following: the delivery pressure at the injection orifice, the size and shape of the injector orifice, the volume of injectate delivered, the distance of the injection orifice from the internal urethral tissue at injection, and the amount of pressure or tension placed on the internal urethral tissue at the time of injection (e.g., by a tissue tensioner). Generally, higher injection pressure results in deeper penetration of the injectate; a smaller orifice (based on constant injection pressure) results in deeper penetration of the injectate; and a reduced distance between orifice and tissue results in deeper penetration of the injectate.

Methods of treatment can include one or multiple discrete steps relating to insertion of an injector device as described herein; positioning of the device to place one or more injection orifices at desired locations within the prostatic urethra; optionally, actuation of a tissue tensioner; optionally, use of an optic device; transurethral injection of an injectate using a needleless mechanism; optionally, one or multiple steps of re-positioning of one or more injection orifices; optionally, one or more additional steps of transurethral injection.

Some steps may differ or be included or excluded from specific methods of treatment, or may be used with small or significant variations, depending on the type of injector device and specific features of the device. For example, an insertion step may differ for a rigid-shaft device and a flexible-shaft device—a flexible shaft (e.g., an injection catheter) may be inserted through the external opening of the urethra (the meatus) whereas a rigid shaft device may require an external incision and a tissue path that leads to the urethra. A device that includes a multi-component shaft may be inserted by multiple steps, i.e., one for each component of the multi-component shaft, whereas a device that includes an integral shaft is inserted as a single unit. A method of using a device that includes multiple stationary injection orifices may involve an injection from each of the orifices, whereas a method of using a device that includes a moveable injection orifice may include steps of making an injection, moving the injection orifice, and making another injection.

During an injection step, a needleless injector device causes a volume of injectate to be ejected from an injection orifice as a fine, high-pressure stream. The stream passes through tissue, e.g., through the urethra and into the prostate. The stream can become dispersed into tiny droplets that travel separately and disperse throughout the injected tissue. Ultimately, the injectate becomes distributed as a fine mist of tiny particles that enter and travel over a range of depths and directions into the injected tissue (e.g., prostate), to produce a "cloud"-type penetration of the injectate throughout the tissue. Each particle of injectate can preferably remain within the injected tissue, although when injecting the prostate, a portion of a total amount of particles may become located within gland ducts where that portion of injectate could flow to the urethra. As opposed to the use of a needle, the injectate of the needleless procedure does not pool at one location and does not require a slow injection rate. Also, even though a portion of the injected particles may arrive at a location that includes a gland duct, the possibility that those particles will flow from an injected prostate and to the urethra is relatively small because the particles are sufficiently dispersed that they may not collect to sufficient volume to produce a flow.

The injectate may be characterized in terms of any one or more of the following: volume of individual injections; volume total injectate: size of dispersed particles (e.g., average size); and the dispersal pattern, including directional dispersion, depth of individual particles, and average depth. These factors can be affected or controlled as desired, by selecting features or operating parameters of the injection step itself. Specifically, above-referenced features can be affected and controlled by adjusting one or more of: the injection pressure; injection volume; number of injections; distance from the injection orifice to tissue at injection; and the type of injection orifice.

Briefly, a TEAP procedure may be performed using a needleless injector device such as illustrated or described herein, or using devices that are similar or analogous to those illustrated or described.

Figure 8:
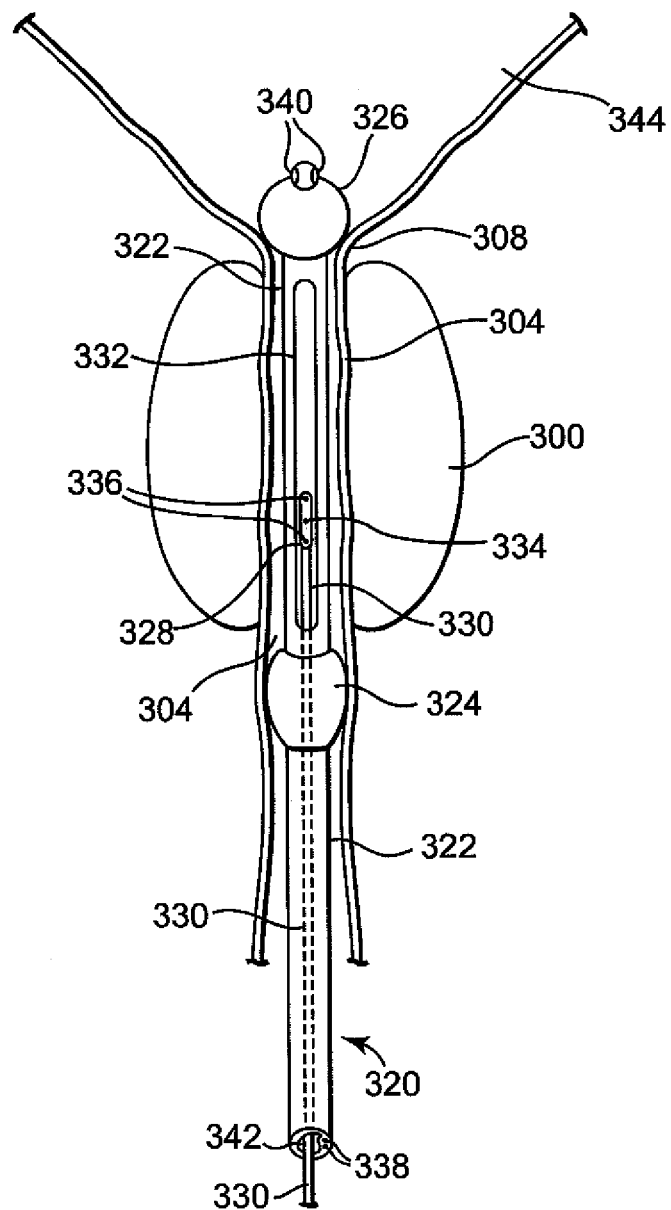
FIGS. 8 and 9 illustrate exemplary injector devices as installed during use.

FIG. 8 illustrates a method involving a flexible-shaft injection catheter to inject fluid into a prostate. Injection catheter 320 includes a distal end that includes a portion of shaft 322 positioned within prostatic urethra 304, and a proximal end (not shown) that remains external to the patient. Injection catheter 320 also includes positioning features in the form of proximal and distal balloons 324 and 326, respectively, at locations along shaft 322. Moveable injector head 328 is located at the end of moveable injection shaft 330. Moveable injection shaft 330 is flexible and moveable along a length of shaft 322, to allow movement of injector head 328 within slot 332 of shaft 322. Injector head 328 is illustrated to include injection orifice 334 and vacuum orifices 336, each of which is in fluid communication with a proximal end of device 320 through lumens (not shown) within a length of moveable injection shaft 330. Proximal and distal balloons 324 and 326 are in fluid communication with the proximal end of device 320 through lumens 338 defined by the sidewall of shaft 322. Drainage apertures 340 are located at the end of shaft 322 to be inside of bladder 344 when device 320 is installed, and are in communication with the proximal end of device 320 through drainage lumen 342.

In use, shaft 322 is advanced into position within urethra 304 such that injector head 328 is within prostatic urethra 304. This can be done by inserting flexible shaft 322 through the external orifice of the urethra (meatus) or by preparing an external incision and a tissue path leading to the prostatic urethra. To identify and fix the proper internal location of shaft 322 and injection orifice 328 within urethra 304, distal balloon 326 becomes located within bladder neck 308 and proximal balloon 324 becomes located at the proximal end of prostatic urethra 304, optionally sealing the ends of prostatic urethra 304. The space within prostatic urethra 304 between proximal balloon 324 and distal balloon 326 can be referred to as the zone of treatment.

According to this embodiment of a needleless injector device and method of treatment, injection catheter 320 does not include an optical feature to view injection orifice 334 during positioning or use, or to otherwise allow placing injection orifice 334 or injector head 328 at a desired location within prostatic urethra 304 during installation and treatment. Instead, injection catheter 320 can be used by a "blind delivery" method that places injector head 328 and injection orifice 334 at desired locations within prostatic urethra 304 by use of distal and proximal balloons 326 and 324, in combination with knowledge of the dimensions of the features device 320 such as the distances between balloons 324 and 326 and the distances from balloons 324 and 326 to distal and proximal ends of slot 332.

FIG. 8 illustrates device 320 that includes a moveable injector head 328 that can allow for injection of injectate fluid at different positions of prostatic urethra 304, when installed. Alternately, according to other variations of device 320, shaft 322 may include multiple injection orifices along the length of shaft 322 within the zone of treatment, or around the perimeter of shaft 322 within the zone of treatment.

Once shaft 322 is positioned within prostatic urethra 304 as illustrated, injection catheter 320 is used to deliver one or multiple transurethral injections of injectate using a needleless mechanism that includes injection orifice 334. The procedure may include one or multiple steps of re-positioning injector head 328 by moving injector head 328 within slot 332 to treat all portions of a prostate.

Figure 9:
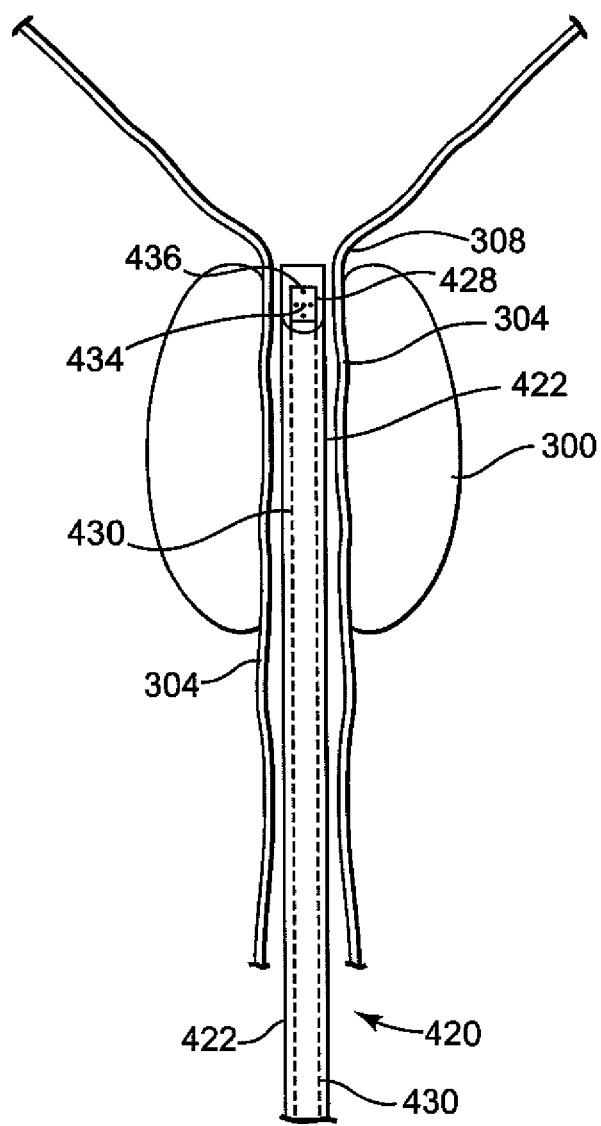

FIG. 9 illustrates a method using a rigid, e.g., multi-piece shaft, needleless injector device to inject fluid transurethrally into a prostate. As illustrated, device 420 includes a distal end that includes a portion of shaft 422 positioned within prostatic urethra 304. A proximal end (not shown) of the device remains external to the patient. Device 420 as illustrated does not include a positioning feature such as a balloon along shaft 422, although a balloon or other positioning feature may optionally be included at any desired location along shaft 422. Device 420 may include an endoscope (not shown) that allows viewing of injector head 428 during use. Injector head 428 is located at the end of injection shaft 430. Injector head 428 includes injection orifice 434 located at the center of injection head 428 and four vacuum orifices 436 located to surround injection orifice 434. Each of injection orifice 434 and vacuum orifices 436 is in fluid communication with a proximal end of device 420 through lumens (not shown) within a length of injection shaft 430.

In use, shaft 422 is advanced into position within urethra 304 such that injector head 428 is within prostatic urethra 304. This can be done by inserting shaft 422 through an external incision and tissue path leading to urethra 304. An endoscope optionally included as part of device 420 can be used to view the location of injection head 428 relative to prostatic urethra 304, to identify and properly locate injection orifice 428.

FIG. 9 illustrates device 420 that includes injector head 428 that can allow for injection of fluid at different positions of prostatic urethra 304, when installed, by moving shaft 422 to different locations along the length of prostatic urethra 304. At each desired location, injection head 428 is positioned as desired and suction is pulled though vacuum orifices 436 to cause the internal surface of prostatic urethra 304 to contact the surface of injection head 428. Device 420 is then actuated to deliver a transurethral injection from injection orifice 434, through prostatic urethra 304, and into prostate 300. The procedure may include one or multiple steps of positioning or re-positioning injector head 428 by moving injector head 428 within prostatic urethra 304. Alternately, according to other variations of device 420, shaft 422 may include multiple injection orifices along the length of shaft 422 or around the perimeter of shaft 422.

A chemical ablation technique according to this description can allow for delivery of reduced dosages of therapeutic agent, e.g., a drug, other pharmaceutical agent, or ethanol or other ablative fluid, relative to other methods that involve injection of therapeutic agent using a needle. In general, a total amount of therapeutic agent, e.g., ethanol, injected into a prostate will depend on a variety of factors including, e.g., the size of the prostate to be treated, the shape of the prostate (i.e., length and width), the number of injection sites required, whether the median lobe is enlarged, and the nature and degree of prostate disease. A number of methodologies can be used to estimate prostate volume, including magnetic resonance imaging (MRI), transrectal ultrasonography (TRUS), digital rectal examination (DRE), and serum prostate specific antigen (PSA) level. Ethanol or another therapeutic agent may be delivered by multiple injections at multiple injection sites, with the size of each injection and the number of injection sites varying according to surgeon preferences.

Where ethanol is used to chemically ablate prostate tissue, medical-grade ethanol (also known as anhydrous alcohol, absolute alcohol, or absolute ethyl alcohol) should be used in the treatment regimens, devices, and products according to the invention. For example, 190-200 proof ethanol that meets guidelines established by the United States Pharmacopeia/National Formulary (USP/NF) is a suitable chemoablation fluid in the treatment regimens of the invention.

Optionally, a chemoablation fluid may be combined with an additive that enhances delivery or distribution of the chemoablation fluid within prostate tissue, or that enhances the efficacy of the chemoablation fluid. The additive may be incorporated to disperse the chemoablation fluid in the vasculature of the prostate tissue more effectively, or it may be incorporated to retain the chemoablation fluid within the prostate tissue and avoid extravasation beyond prostate tissue (i.e., beyond the prostatic capsule).

Suitable alternative chemical ablation agents include toxins whose effect can be substantially contained to the tissue to be ablated. By way of example, other alcohols, certain enzymatic solutions, and some antibiotics may be suitable agents for chemically ablating prostate tissue. In addition, other dehydrating solutions such as concentrated saline solution may also be suitable chemoablation agents. As an example of a suitable alcohol, phenol (carbolic acid) has been injected prostatically to ablate prostate tissue as a treatment for BPH. A sterile aqueous mixture of phenol, glacial acetic acid, and glycerine has been used.

While the above description specifically describes apparatus and methods of treating the prostate, the invention can also relate to treatment of other tissue of the lower urinary tract, either in females or males. For example, the apparatus of the invention may be useful to inject the urethral tissue itself or the external sphincter, as opposed to passing through the ureteral tissue. Further, an injectate other than an ablative material may be injected into tissue of the lower urinary tract (e.g., bladder, urethra, kidneys, ureters, prostate, etc.) such as individual or combination treatments using drugs or other therapeutic agents, e.g., botulism toxin ("botox"), an antiandrogen, among others as will be understood. Advantages of a needleless injection of an active pharmaceutical agent is local placement of the agent to avoid systemic side effects. Specific examples of active pharmaceutical agents that may be injected include Botulism Toxin types A through G; 5-alpha reductase inhibitors such as dutasteride and finasteride; alpha blockers such as alfuzosin, doxazosin, prazosin, tamsulosin hydrochloride, terazosin, to treat BPH; or any of various antibiotics (e.g., to treat prostatitis) and analgesics.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

The invention claimed is:

1. A needleless injector comprising:
a body comprising a fluid chamber;
an outer shaft extending from an outer shaft proximal end at the body to an outer shaft distal end, the outer shaft comprising an outer shaft lumen between the outer shaft proximal end and the outer shaft distal end, to accommodate an injection shaft;
an injection shaft located within the outer shaft lumen and moveable lengthwise, rotationally, or lengthwise and rotationally, within the outer shaft lumen, the injection shaft comprising an injection shaft proximal end, an injection shaft distal end, an injection shaft terminus, and an injection lumen extending between the injection shaft proximal end and the injection shaft distal end,
an injection orifice at the distal end of the injection shaft and in fluid communication with the fluid chamber through the injection lumen, the injection orifice being located on a proximal side of the injection shaft terminus and being positioned for fluid ejection in a lateral direction relative to a longitudinal axis of the injection shaft at the location of the injection orifice, wherein the injection orifice is proximally located relative to the outer shaft distal end;
a pressure source in communication with the fluid chamber, the pressure source being capable of pressurizing fluid within the fluid chamber to an injection pressure capable of causing fluid ejected from the injection orifice to penetrate into tissue; and
an optical device that allows viewing a location at a distal end of the device,
wherein the outer shaft further comprises a slot, and wherein the injection orifice is positionable for fluid ejection in the lateral direction through the slot of the outer shaft.

2. A needleless injector according to claim 1, wherein the pressure source is capable of pressurizing fluid within the fluid chamber to an injection pressure capable of causing fluid ejected from the injection orifice to pass through a tissue surface and become dispersed within tissue as droplets.

3. A needleless injector according to claim 1, wherein the injection shaft includes multiple injection orifices on a proximal side of the injection shaft terminus.

4. A needleless injector according to claim 1, wherein the injection pressure is 2000 pounds per square inch or greater.

5. A needleless injector according to claim 1, wherein the outer shaft is flexible and the injection shaft is flexible.

6. A needleless injector according to claim 1, wherein:
the pressure source is capable of pressurizing fluid within the fluid chamber to an injection pressure capable of causing fluid ejected from the injection orifice to pass through a tissue surface and become dispersed within tissue as droplets;
the outer shaft is flexible; and
the injection shaft is flexible.

7. A needleless injector according to claim 1, wherein:
the injection pressure is 2000 pounds per square inch or greater;
the outer shaft is flexible; and
the injection shaft is flexible.

* * * * *